United States Patent
Strisovsky et al.

(10) Patent No.: US 10,927,146 B2
(45) Date of Patent: Feb. 23, 2021

(54) PEPTIDYL KETOAMIDES AS INHIBITORS OF RHOMBOID PROTEASES

(71) Applicant: USTAV ORGANICKE CHEMIE A BIOCHEMIE AV CR, V.V.I., Prague (CZ)

(72) Inventors: Kvido Strisovsky, Hostivice (CZ); Pavel Majer, Prague (CZ); Stanco Stancev, Prague (CZ); Anezka Ticha, Telc (CZ)

(73) Assignee: USTAV ORGANICKE CHEMIE A BIOCHEMIE AV CR, V.V.I., Prague (CZ)

( * ) Notice: Subject to any disclaimer, the term of this patent is extended or adjusted under 35 U.S.C. 154(b) by 0 days.

(21) Appl. No.: 16/619,036

(22) PCT Filed: Jun. 12, 2018

(86) PCT No.: PCT/CZ2018/050034
§ 371 (c)(1),
(2) Date: Dec. 3, 2019

(87) PCT Pub. No.: WO2018/228617
PCT Pub. Date: Dec. 20, 2018

(65) Prior Publication Data
US 2020/0095278 A1 Mar. 26, 2020

(30) Foreign Application Priority Data
Jun. 12, 2017 (GB) ..................... 1709317

(51) Int. Cl.
*C07K 5/02* (2006.01)
*A61P 33/06* (2006.01)
*A61K 38/08* (2019.01)
*A61K 38/00* (2006.01)

(52) U.S. Cl.
CPC ............ *C07K 5/0202* (2013.01); *A61K 38/08* (2013.01); *A61P 33/06* (2018.01); *A61K 38/00* (2013.01)

(58) Field of Classification Search
None
See application file for complete search history.

(56) References Cited

FOREIGN PATENT DOCUMENTS

| WO | 9817679 A1 | 4/1998 |
|---|---|---|
| WO | 9964442 A1 | 12/1999 |

OTHER PUBLICATIONS

Li, Zhaozhao et al; "Novel peptidyl alpha-keto amide inhibitors of calpains and other cysteine proteases." J. Med. Chem. (1996) 39 p. 4089-4098.*
Kher et al., "Substrate derived peptidic-ketomaides as inhibitors of the malarial protease PfSUB1", Bioorganic and Medicinal Chemistry Letters, vol. 24, No. 18, Jan. 1, 2014 (Jan. 1, 2014), pp. 4486-4489.
Venkatraman, Srikanth et al: "Design and Synthesis of Depeptidized Macrocyclic Inhibitors of Hepatitis C NS3-4A Protease Using Structure-Based Drug Design", Journal of Medicinal Chemistry, vol. 48, No. 16, Aug. 1, 2005 (Aug. 1, 2005), pp. 5088-5091.
Wolf Eliane Vet al: "Inhibitors of rhomboid proteases", Biochimie, Masson, Paris, FR, vol. 122, Jul. 10, 2015 (Jul. 10, 2015), pp. 38-47.
Nagai et al: "Postatin, a new inhibtior of prolyl endopeptidase, produced by Streptomyces viridochromogenes MH534-30F3. II.Structure determination and inhibitory activities",The Journal of Antibiotics, Nature Publishing Group, GB, vol. 44, No. 9,Sep. 25, 1991 (Sep. 25, 1991), pp. 956-961.
Kher et al., "Substrate derived peptidic-ketomaides as inhibitors of the malarial protease PfSUB1", Bioorganic and Medicinal Chemistry Letters, vol. 24, No. 18, Jan. 1, 2014 (Jan. 1, 2014), pp. 4486-4489, abstract only.
Venkatraman, Srikanth et al: "Design and Synthesis of Depeptidized Macrocyclic Inhibitors of Hepatitis C NS3-4A Protease Using Structure-Based Drug Design", Journal of Medicinal Chemistry, vol. 48, No. 16, Aug. 1, 2005 (Aug. 1, 2005), pp. supplemental results only, s1-s20.
Talanian, R V et al: "Caspases as targets for anti-inflammatory and anti-apoptotic drug discovery", Journal of Medicinal Chemistry, American Chemical Society, vol. 43, No. 18, Sep. 7, 2000 (Sep. 7, 2000), pp. 3351-3371, first page only.
Cho Sangwoo et al: "Crystal Structures and Inhibition Kinetics Reveal a Two-Stage Catalytic Mechanism with Drug Design Implications for Rhomboid Proteolysis", Molecular Cell, Elsevier, Amsterdam, NL, vol. 61, No. 3, Jan. 21, 2016 (Jan. 21, 2016), pp. 329-340.
Wolf Eliane Vet al: "Inhibitors of rhomboid proteases", Biochimie, Masson, Paris, FR, vol. 122, Jul. 10, 2015 (Jul. 10, 2015), pp. 38-47, abstract only.
Ticha Anezka et al: "General and Modular Strategy for Designing Potent, Selective, and Pharmacologically Compliant Inhibitors of Rhomboid Proteases", Cell Chemical Biology, vol. 24, No. 12, Dec. 21, 2017 (Dec. 21, 2017), p. 1523.

* cited by examiner

*Primary Examiner* — Fred H Reynolds
(74) *Attorney, Agent, or Firm* — Notaro, Michalos & Zaccaria P.C.

(57) ABSTRACT

Compounds useful for the treatment of malaria, cancer, Parkinson's disease, diabetes, and bacterial infection.

14 Claims, 3 Drawing Sheets
Specification includes a Sequence Listing.

A

B

PEPTIDYL KETOAMIDES AS INHIBITORS OF RHOMBOID PROTEASES

FIELD OF THE INVENTION

The invention relates to a class of chemical compounds, compositions comprising such compounds, methods for their synthesis, and their use in the therapy of various maladies.

BACKGROUND ART

Rhomboid intramembrane proteases (EC 3.4.21.105, Pfam PF01694) are evolutionarily widespread and fulfil important biological functions including growth factor secretion, regulation of mitochondrial dynamics, and membrane protein quality control. They are increasingly being explored as potential drug targets, for example for malaria (Baker et al., 2006, Lin et al., 2013, O'Donnell et al., 2006), cancer (Song et al., 2015), Parkinson's disease (Meissner et al., 2015), diabetes (Chan et al., 2013) and potentially for the control of infections by extraintestinal pathogenic *Escherichia coli* or related bacteria (Russell et al., 2017). In contrast to the promising roles of rhomboid proteases in disease contexts, selective and potent rhomboid inhibitors that could serve for cell biological studies, validation of therapeutic potential of rhomboids and as templates for drug development, are lacking.

The currently known inhibitors of rhomboid proteases suffer from numerous drawbacks making them unsuitable for use in cell biology or as templates for drug development. Isocoumarins (Vosyka et al., 2013) are irreversible inhibitors, are reactive towards many other serine hydrolases (Boehm/chin et al., 2014) and thus lack selectivity for rhomboids. β-lactams are not very active in vivo ($EC_{50}$ ~5-10 µM) (Pierrat et al., 2011), β-lactones are not very potent (apparent $IC_{50}$ of ~40 µM) (Wolf et al., 2013), and both are slowly turned over by the enzyme. Furthermore, for these inhibitor classes, a rational strategy to modulate selectivity for rhomboids is not available.

The principles of catalytic mechanism and substrate specificity of a protease determine to a large extent the strategies for inhibitor development. Rhomboids are serine proteases with a Ser-His catalytic dyad (Wang et al., 2006), and recognise their transmembrane substrates in a two-tier process. It is assumed that first a portion of the transmembrane domain of the substrate docks into an intramembrane interaction site of rhomboid within the plane of the lipid bilayer, upon which a linear segment of the substrate interacts with the water-exposed active site (reviewed in Strisovsky, 2013, Strisovsky, 2016). This 'recognition motif' encompasses the P4 to P2' residues of the substrate (Strisovsky et al., 2009), it largely determines the $k_{cat}$ of the reaction (Dickey et al., 2013) and thus modulates selectivity towards a given rhomboid protease (Ticha et al., 2017). Recent reports have shown that peptidyl chloromethylketones (Zoll et al., 2014) and peptidyl aldehydes (Cho et al., 2016) are weak inhibitors of rhomboid proteases at medium to high micromolar concentrations. However, these classes of compounds lack selectivity and their potency is insufficient for their use as research tools.

There are now disclosed novel potent and selective rhomboid inhibitors based on a modular scaffold of sequence-optimised peptidyl-ketoamide substituted with large hydrophobic substituent. The inhibitors disclosed are useful in the treatment of a variety of indications associated with rhomboid proteases, for example, malaria, Parkinson's disease and cancer.

DISCLOSURE OF THE INVENTION

In a first aspect, the invention provides compounds of the formula (I)

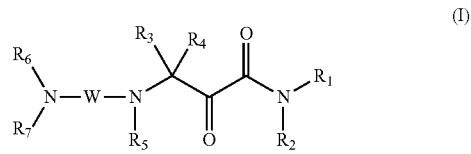

wherein $R_1$ is selected from the group consisting of H, alkyl, haloalkyl, alkenyl, alkynyl, aryl, arylalkyl, cycloalkyl, cycloalkylalkyl, cycloalkenyl, cycloalkenylalkyl, heterocyclyl, heterocyclylalkyl, heteroaryl and heteroarylalkyl, each optionally substituted with from 1 to 3 substituents independently selected from the group consisting of alkyl, cyano, halo, oxo, nitro, hydroxyl, —O(alkyl), —$NH_2$, —N(H)(alkyl), —N(alkyl)$_2$, —S(alkyl), —S(O)(alkyl), —$SO_2$alkyl, —$NHCONH_2$, —$CO_2H$, —$CO_2$(alkyl), —CO-alkyl, —$CONH_2$, —CONH-alkyl;

$R_2$ and $R_5$ are selected from hydrogen and alkyl;

or, taken together with the atoms to which they are attached, $R_1$ and $R_2$ or $R_1$ and $R_3$ form a heterocyclyl ring;

$R_3$ and $R_4$ are independently selected from the group consisting of hydrogen, alkyl, haloalkyl, alkenyl, alkynyl, aryl, arylalkyl, cycloalkyl, cycloalkylalkyl, cycloalkenyl, cycloalkenylalkyl, heterocyclyl, heterocyclylalkyl, heteroaryl and heteroarylalkyl; or, taken together with the carbon atom to which they are attached, $R_3$ and $R_4$ form a cycloalkyl or heterocyclyl ring; wherein each $R_3$ and $R_4$, is independently optionally substituted with from 1 to 3 substituents independently selected from the group consisting of alkyl, cyano, halo, oxo, nitro, hydroxyl, —O(alkyl), —$NH_2$, —N(H)(alkyl), —N(alkyl)$_2$, —S(alkyl), —S(O)(alkyl), —$SO_2$-alkyl, —$NHCONH_2$, —$CO_2H$, —$CO_2$-(alkyl), —COalkyl, —$CONH_2$, —CONH-alkyl and —CON(alkyl)$_2$;

$R_6$ and $R_7$ are independently selected from the group consisting of hydrogen, alkyl, cycloalkyl, acyl, aryl, heteroaryl, and heterocyclyl; or, taken together with the carbon atom to which they are attached, $R_6$ and $R_7$ form a cycloalkyl or heterocyclyl ring;

W represents

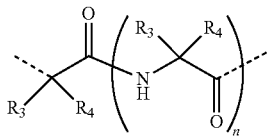

n is an integer of from 0 to 20;

optionally any $R_3$ or $R_4$ can form a ring with $R_1$ or $R_2$;

or a pharmaceutically acceptable salt, ester or prodrug thereof.

According to a second aspect, the invention provides a pharmaceutical composition comprising a compound of formula (I) together with a pharmaceutically acceptable excipient.

According to a third aspect, the invention provides a compound of formula (I) or a composition according to the second aspect for use in therapy.

According to a fourth aspect, the invention provides a compound of formula (I) or a pharmaceutical composition according to the second aspect for use in the treatment of a condition selected from malaria, cancer, Parkinson's disease, diabetes, and bacterial infection.

According to a fifth aspect, the invention provides a method of treatment of a condition selected from malaria, cancer, Parkinson's disease, diabetes, and bacterial infection comprising administering to a patient
in need thereof a compound of formula (I) or a pharmaceutical composition according to the second aspect.

DETAILED DESCRIPTION OF THE PREFERRED EMBODIMENTS

Figure 1:
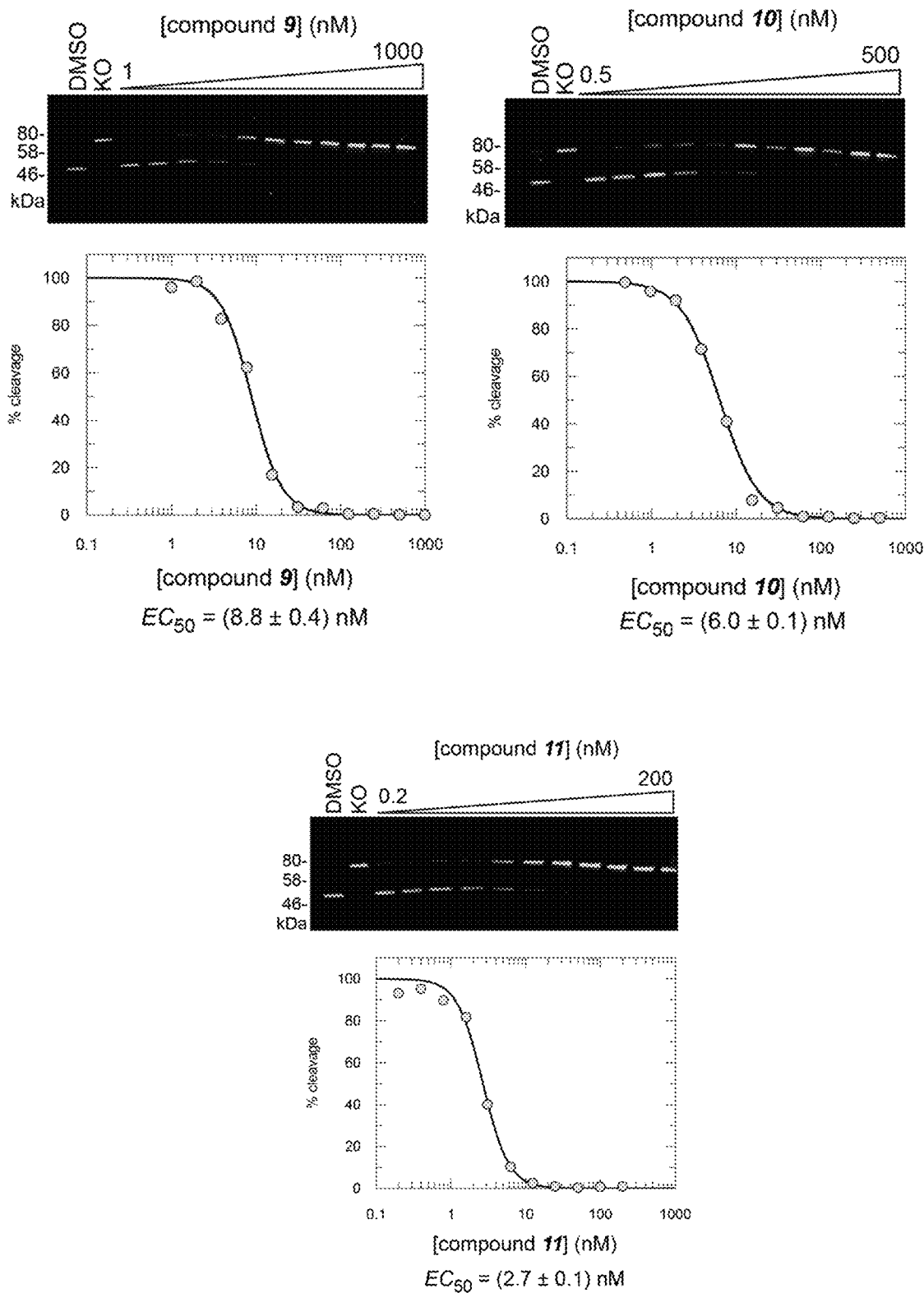
FIG. 1 is a series of graphs showing in vivo inhibition of *E. coli* rhomboid GlpG by compounds 9, 10 and 11. Cleavage of substrate MBP-FLAG-LacYTM2-Trx (Strisovsky et al., 2009) expressed in wild type *E. coli* NR698 (Ruiz et al., 2005) in the presence of increasing concentrations of inhibitors was evaluated by immunoblotting for FLAG and detection by near-infrared fluorescence. DMSO, dimethylsulfoxide vehicle control; KO, *E. coli* glpG::tet.

Provided herein are potent and selective covalent reversible inhibitors of rhomboid intramembrane proteases, being peptidyl-ketoamides of the general formula (I). The molecules comprise two moieties; the first is a peptidyl part, and the second is the tail substituent at the ketoamide nitrogen.

A preferred subset of compounds of the invention have the formula (II)

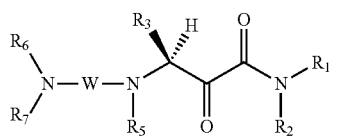

(II)

wherein $R_3$ is $C_1$-$C_6$ alkyl, and $R_1$, $R_2$, $R_5$-$R_7$ and W have the meanings ascribed elsewhere herein.

Preferably, $R_2$ is hydrogen.

Preferably, $R_1$ is selected from the group consisting of alkyl, cycloalkyl, arylalkyl optionally substituted on the aryl ring with from 1 to 3 $C_1$-$C_3$ alkyl substituents, and alkoxycarbonylalkyl.

In some embodiments, $R_1$ is alkyl. More preferably, $R_1$ is $C_1$-$C_6$ alkyl. More preferably, $R_1$ is isopropyl, pentyl or pivaloyl.

In alternative embodiments, $R_1$ is cycloalkyl. More preferably, $R_1$ is $C_3$-$C_7$ cycloalkyl. Still more preferably, $R_1$ is cyclohexyl.

In alternative, preferred embodiments, $R_1$ is arylalkyl. More preferably, $R_1$ is phenylalkyl or naphthylalkyl. Still more preferably, $R_1$ is phenyl($C_1$-$C_6$)alkyl. In such embodiments, the aryl moiety may optionally be substituted with from 1 to 3 substituents independently selected from $C_1$-$C_3$ alkyl, halogen, $C_1$-$C_3$ haloalkyl and $C_1$-$C_3$ alkoxy; methyl is preferred. Explicitly preferred groups $R_1$ of this type are phenylmethyl, 1-phenylethyl, 2-phenylethyl, (2,5-dimethylphenyl)methyl, and 4-phenyl-n-butyl.

In certain preferred embodiments, $R_1$ is alkoxycarbonylalkyl. More preferably, $R_1$ is ($C_1$-$C_6$)alkoxycarbonyl($C_1$-$C_6$) alkyl. More preferably, $R_1$ is ethoxycarbonylmethyl.

W represents a group comprising amino acid residues. The term "amino acid" refers to naturally occurring and non-natural amino acids, as well as amino acid analogues and amino acid mimetics that function in a manner similar to the naturally occurring amino acids. Naturally encoded amino acids are the twenty common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. The term "amino acid analogues" refers to compounds that have the same basic chemical structure as a naturally occurring amino acid, i.e., a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Preferred groups W are (Aaa)$_m$-Arg-His, wherein m represents an integer of from 0 to 18. More preferred are those compounds wherein W represents a group (Aaa)$_p$-Val-Arg-His; and p represents an integer of from 0 to 17. More preferred are those compounds wherein W represents a group (Aaa)$_q$-Arg-Val-Arg-His (SEQ ID NO. 1); and q represents an integer of from 0 to 16.

Preferred groups W are (Aaa)$_m$-Trp-His, wherein m represents an integer of from 0 to 18. More preferred are those compounds wherein W represents a group (Aaa)$_p$-Val-Trp-His; and p represents an integer of from 0 to 17. More preferred are those compounds wherein W represents a group (Aaa)$_q$-Arg-Val-Trp-His (SEQ ID NO. 2); and q represents an integer of from 0 to 16. Most preferably, ($R_6$)($R_7$)N—W— is Acetyl-Arg-Val-Trp-His- (SEQ ID NO. 2 for the amino acid sequence).

"Aaa" means an amino acid. (Aaa)$_m$ means m aminoacids which are independently selected from amino acids and amino acid analogues, (Aaa)$_p$ means p aminoacids which are independently selected from amino acids and amino acid analogues, (Aaa)$_q$ means q aminoacids which are independently selected from amino acids and amino acid analogues.

In some preferred embodiments, n is an integer of from 2 to 15, more preferably 3 to 10, more preferably 4, 5 or 6, most preferably 4. In an especially preferred embodiment, W is Arg-Val-Arg-His.

$R_6$ is preferably selected from the group consisting of alkyl, cycloalkyl, acyl. More preferably, $R_6$ is acyl (most preferably acetyl (ethanoyl)).

Preferably, $R_7$ is hydrogen.

Definitions

As used herein, the term "alkyl," unless otherwise specified, refers to a saturated straight or branched hydrocarbon chain of preferably $C_1$ to $C_6$, and specifically includes methyl, ethyl, propyl, isopropyl, butyl, isobutyl, t-butyl, pentyl, isopentyl, neopentyl, hexyl, isohexyl, cyclohexyl, cyclohexylmethyl, 3-methylpentyl, 2,2-dimethylbutyl, and 2,3-dimethylbutyl, and the like.

The term "alkenyl" as used herein refers to a branched or straight, unsaturated aliphatic group containing at least one carbon-carbon double bond which may occur at any point along the chain. The alkenyl radical may be optionally substituted independently with one or more substituents described herein, and includes "E" and "Z" orientations. Representative examples of alkenyl groups include, but are not limited to, ethenyl, E- and Z-pentenyl, decenyl and the like. Preferred alkenyl groups have 2 to 6 carbon atoms.

The term "alkynyl" as used herein refers to a branched or straight, unsaturated aliphatic group containing at least one carbon-carbon triple bond which may occur at any point along the chain. The alkynyl radical may be optionally substituted independently with one or more substituents described herein. Representative examples of alkenyl groups include, but are not limited to, ethynyl, pent-1-ynyl, and the like. Preferred alkynyl groups have 2 to 6 carbon atoms.

The term "arylalkyl," as used herein, refers to an aryl group, as defined herein, appended to the parent molecular moiety through an alkyl group, as defined above. Representative examples of arylalkyl include, but are not limited to, benzyl, 2-phenylethyl, 3-phenylpropyl, 4-phenylbutyl, 2-naphth-2-ylethyl, and the like.

The term "cycloalkyl", as used herein, refers to a saturated cyclic hydrocarbon group. Representative examples of cycloalkyl include, but are not limited to, cyclopropyl, cyclobutyl, cyclopentyl, cyclohexyl, cycloheptyl, cyclooctyl and the like. Preferred cycloalkyl groups have 3 to 7 carbon atoms.

The term "cycloalkenyl", as used herein, refers to a cyclic hydrocarbon group having at least one ring double bond. Representative examples of cycloalkenyl include, but are not limited to, cyclopentenyl, cyclohexenyl, cycloheptenyl, and the like. Preferred cycloalkenyl groups have 4 to 7 carbon atoms.

The term "cycloalkylalkyl," as used herein, refers to a cycloalkyl group, as defined above, appended to the parent molecular moiety through an alkyl group, as defined above. Representative examples of cycloalkylalkyl include, but are not limited to, cyclohexylmethyl, 2-(cyclopentyl)ethyl, 3-(cyclopropyl)propyl, 2-(cycloheptyl)ethyl, and the like.

The term "cycloalkenylalkyl," as used herein, refers to a cycloalkenyl group, as defined above, appended to the parent molecular moiety through an alkyl group, as defined above. Representative examples of cycloalkenylalkyl groups include, but are not limited to, cyclopentenylmethyl, 1-cyclohexenylethyl, 3-cycloheptenylpropyl, and the like.

As used herein, the term "aryl" refers to aromatic monocyclic or multicyclic groups containing from 5 to 15 carbon atoms. Aryl groups include, but are not limited to groups such as unsubstituted or substituted fluorenyl, unsubstituted or substituted phenyl, and unsubstituted or substituted naphthyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment. Phenyl is preferred.

As used herein the term "heteroaryl" refers to a monocyclic or multicyclic aromatic ring system, in certain embodiments, of 5 to 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

The term "heterocycle" or "heterocyclyl", as used herein, refers to a monocyclic, or bicyclic, group, having from 3 to 10 ring members, unless otherwise specified, containing 1 to 4 heteroatoms selected from N, O, S, SO, $SO_2$, NH or $N(C_1-C_6)$alkyl. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl.

The term "heterocyclylalkyl" as used herein refers to a heterocyclyl group as defined above appended to the parent molecular moiety through an alkyl group, as defined above. Examples are piperazinylmethyl, 2-piperidinylethyl and 3-morpholinylpropyl, 1-(2-furyl)-ethyl, 3-(2-imidazolyl)-propyl and the like.

The term "heteroarylalkyl" as used herein refers to a heteroaryl group as defined above appended to the parent molecular moiety through an alkyl group, as defined above. Examples include 2-pyridylmethyl, 3-pyridylmethyl.

The term "alkoxy," as used herein, refers to an alkyl group, as defined herein, appended to the parent molecular moiety through an oxygen atom. Examples include methoxy, ethoxy, propoxy, isopropoxy, butoxy, isobutoxy, t-butoxy, pentoxy, isopentoxy, neopentoxy, hexyloxy, isohexyloxy, cyclohexyloxy, 2,2-dimethylbutoxy, and 2,3-dimethylbutoxy, and the like.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred. Dihaloalkyl and polyhaloalkyl groups can have two or more of the same halo atoms or a combination of different halo groups within the alkyl. Examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g, trifluoromethyl.

The term "acyl" as used herein means an organic radical having 1 to 6 carbon atoms (branched or straight chain) derived from an organic acid by removal of the hydroxyl group. Examples of acyl groups are methanoyl, ethanoyl, propanoyl, n-butanoyl, pivaloyl, and the like.

Where a group is described as "optionally substituted", for example in the case of aryl, heteroaryl, and heterocyclyl, the substituents are, unless otherwise specified, selected from the group consisting of $C_1$-$C_3$ alkyl, $C_1$-$C_3$ alkoxy, halogen, $C_1$-$C_3$ haloalkyl, $C_1$-$C_3$ haloalkoxy, nitro, cyano, and hydroxyl.

The term "pharmaceutically acceptable salt," as used herein, refers to salts that are known in the pharmaceutical art. Compounds of the invention may be acidic or basic in nature, and hence may form salts with bases or acids respectively. Examples of pharmaceutically acceptable salts are those formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid. Examples of salts formed with bases include metal salts such as sodium, potassium, magnesium or calcium salts or amino salts such as ammonium, triethylamine salts, and the like, all of which may be prepared according to conventional methods.

The term "prodrug" as used herein, represents those derivatives of the compounds of the present invention which are metabolised in vivo to yield compounds of formula (I).

As used herein, "protecting group" refers to a group that is joined to a reactive group (e.g., a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example (Wuts et al., 2014), which is incorporated by reference herein in its entirety. The term "protection" refers to the introduction of such a group, and the term "deprotection" to its removal. The term "protected" refers to a molecule comprising such a group.

Pharmaceutically acceptable esters include $C_1$-12 alkyl esters.

Synthesis of Compounds

Suitable methodologies for the preparation of α-ketoamides are disclosed in (De Risi et al., 2016). The subject compounds of formula (I) may be prepared according to Scheme I

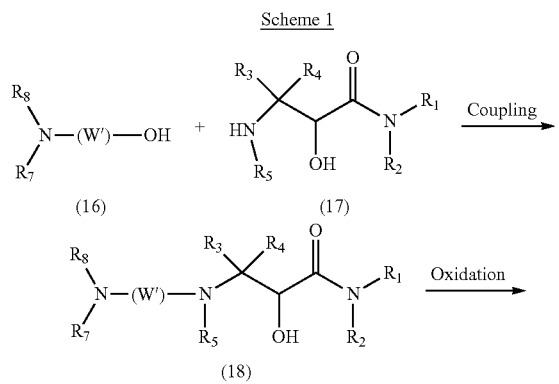

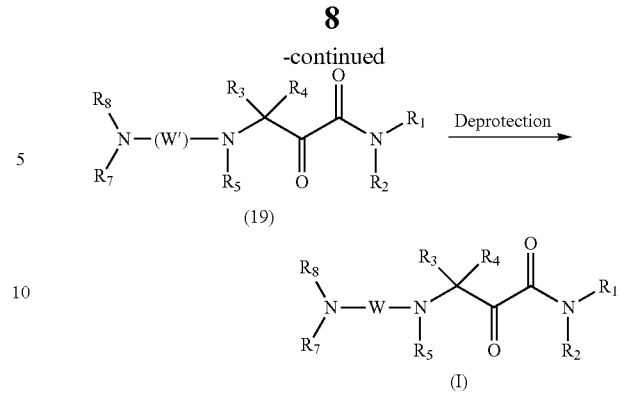

Protected peptide (16) wherein $R_6$ and $R_7$ are as defined above, and W' represents a group W as defined above, wherein none, or one or more, or all of the amino acids Aaa is independently protected with a protecting group, is reacted with α-hydroxy-β-aminoamide (17) under suitable peptide coupling conditions. Suitable conditions will be known to those skilled in the art, and are set out, for example in (Lloyd-Williams et al., 1997). Suitable coupling agents include: carbodiimide reagents, such as DCCI, PriN=C=NPri, EtN=C=N(CH$_2$)$_3$NMe$_2$, HCl; isoxazolium reagents, such as those of Woodward and Kemp; acyloxyphosphonium reagents, such as BOP, PyBOP, PyBrOP/HOBt/DIEA and TFCH/; acyloxyuronium reagents, e.g. TBTU, HBTU, HATU; acid fluorides; and the like.

Protected peptidyl-α-hydroxyamide (18) is oxidized to give protected peptidyl-α-ketoamide (19). Suitable oxidation conditions include Swern Oxidation, Dess-Martin's Periodinane or other methods as described (Hudlicky, 1990).

Finally, protected peptidyl-α-hydroxyamide (18) is subjected to deprotection to yield the target compound (I).

The skilled person will be aware of methods for the preparation of peptide (16). This are also extensively discussed in (Lloyd-Williams et al., 1997). α-hydroxy-β-aminoamide (17) is suitably prepared by the Passerini reaction, as described (Semple et al., 2000).

Formulations and Administration

The present compound can be administered orally or parenterally. In the case of oral administration, the present compound can be also used as a conventional preparation, for example, as any dosage form of a solid agent such as tablets, powders, granules, capsules and the like; an aqueous agent; an oily suspension; or a liquid agent such as syrup and elixir. In the case of parenteral administration, the present compound can be used as an aqueous or oily suspension injectable, or a nasal drop. Upon preparation of it, conventional excipients, binders, lubricants, aqueous solvents, oily solvents, emulsifiers, suspending agents, preservatives, stabilizers and the like may be arbitrarily used. A preparation of the present invention is prepared by combining (e.g. mixing) a therapeutically effective amount of the present compound with a pharmaceutically acceptable carrier or diluent.

A dose of the present invention is different depending on an administration method, an age, a weight and condition n of a patient, and a kind of a disease and, usually, in the case of oral administration, about 0.05 mg to 3000 mg, preferably about 0.1 mg to 1000 mg may be administered per adult a day, if necessary, by dividing the dose. In addition, in the case of parenteral administration, about 0.01 mg to 1000 mg, preferably about 0.05 mg to 500 mg is administered per adult per day.

While it is possible for the compound of formula (I) to be administered alone, it is preferable to present it as part of a pharmaceutical formulation. Such a formulation will comprise the above defined compound of formula (I) together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art.

Such methods include the step of bringing into association the above defined active agent with the carrier. In general, the formulations are prepared by uniformly and intimately bringing into association the active agent with liquid carriers or finely divided solid carriers or both, and then if necessary shaping the product.

The invention extends to methods for preparing a pharmaceutical composition comprising bringing a compound of Formula (I) or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral. Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term pharmaceutically acceptable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatine and glycerine, or sucrose and acacia; and mouthwashes comprising the active agent in a suitable liquid carrier.

Methods of Treatment

The compounds described herein are useful in the treatment of parasitic infections, in particular malaria. They are believed to exert such effects through their ability to inhibit the growth of or kill the parasitic protozoan which causes malaria (e.g., *P. falciparum*, *P. vivax*, *P. ovale*, and *P. malariae*). The treatment may be curative, preventative or intended to arrest the progress of the disease. In some embodiments, the compounds of formula (I) may be administered with one or more known antimalarial compounds, including chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, and any combination thereof. Certain compounds of the invention may be useful in the treatment of malaria which is resistant to one or more known therapies.

The compounds described herein are useful in the treatment of Parkinson's disease. The treatment may be curative, preventative or intended to arrest the progress of the disease. In some embodiments, the compounds of formula (I) may be administered with one or more known compounds for this indication, including L-DOPA/carbidopa, entacapone, ropinrole, pramipexole, bromocriptine, pergolide, trihexephendyl, and amantadine.

The compounds of the invention are useful in the treatment of cancer. Exemplary cancers that may be treated by the compounds and methods of the invention include, but are not limited to, myeloid leukemia, lymphoblastic leukemia, melanoma, breast, lung, colon, liver, gastric, kidney, ovarian, uterine, and brain tumours.

The compounds of the invention are effective in lowering glucose, lipids, and insulin in diabetic animals and lipids in non-diabetic animals. The compounds are efficacious in the treatment, control and/or prevention of non-insulin dependent diabetes mellitus (NIDDM) in humans and in the treatment, control, and/or prevention of conditions associated with NIDDM.

The compounds of the invention are effective in treating bacterial infections in animals including man, which comprises administering to the afflicted animals an antibacterially effective amount of a compound or a pharmaceutical composition of a compound of the invention.

The compounds of the invention are useful to treat bacterial infections including infections caused by Gram-negative bacterial strains, Gram-positive bacterial strains and multiple drug-resistant bacterial strains.

Gram-negative bacterial strains include *Escherichia coli*, *Caulobacter crescentus*, *Pseudomonas aeruginosa*, *Agrobacterium tumefaciens*, *Branhamella catarrhalis*, *Citrobacter diversus*, *Enterobacter aerogenes*, *Enterobacter cloacae*, *Enterobacter sakazakii*, *Enterobacter asburiae*, *Pantoea agglomerans*, *Klebsiella pneumoniae*, *Klebsiella oxytoca*, *Klebsiella rhinoscleromatis*, *Proteus mirabilis*, *Salmonella typhimurium*, *Salmonella enteriditis*, *Serratia marcescens*, *Shigella sonnei*, *Neisseria gonorrhoeae*, *Acinetobacter baumannii*, *Acinetobacter calcoaceticus*, *Acinetobacter lwoffi*, *Fusobacterium nucleatum*, *Veillonella parvula*, *Bacteroides forsythus*, *Actinobacillus actinomyce-* temcomitans, Aggregatibacter actinomycetemcomitans, Porphyromonas gingivalis, Helicobacter pylori, Francisella tularensis, Yersinia pestis, Borrelia burgdorferi, Neisseria meningitidis and Haemophilus influenza.

Gram-positive bacterial strains include Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Bacillus anthracis, Bacillus cereus, Micrococcus luteus, Mycobacterium tuberculosis, Clostridium difficile, Propionibacterium acnes, Streptococcus mutans, Actinomyces viscosus, Actinomyces naeslundii, Streptococcus sanguis, Streptococcus pneumoniae, Streptococcus viridans and Streptococcus salivarius.

Multiple drug-resistant bacterial strains include methicillin-resistant Staphylococcus aureus, vancomycin-resistant Enterococci, multiple drug-resistant Mycobacterium tuberculosis, and multidrug-resistant Clostridium difficile.

EXAMPLES

List of Abbreviations

Boc—tert-butyloxycarbonyl
Bn—benzyl
$^{13}$C NMR—$^{13}$C nuclear magnetic resonance spectrum
Cy—cyclohexyl
DCM—dichloromethane
DMSO-d$_6$—dimethylsulfoxide hexadeuterated
EGF—epidermal growth factor receptor
eqv.—equivalent
ESI-MS—electrospray ionisation mass spectrometry
Et—ethyl
$^1$H NMR—proton nuclear magnetic resonance spectrum
(RP) HPLC—(reversed phase) high performance liquid chromatography
HR-MS—high resolution mass spectrometry
LC-MS—liquid chromatography mass spectrometry
PARL—presenilin associated rhomboid like
Pbf—2,2,4,6,7-Pentamethyldihydrobenzofuran-5-sulfonyl protecting group
Ph—phenyl
TLC—thin layer chromatography
TGFα—transforming growth factor alpha
TFA—trifluoroacetic acid
Trt—trityl
TCFH—tetramethylchloroformamidinium hexafluorophosphate
DMF—dimethylformamide
DIEA—diisopropylethylamine
PyBrOP—Bromotripyrrolidinophosphonium hexafluorophosphate
HOBt—1-Hydroxybenzotriazole
tBuOH—tert-buthanol
Et3N—trimethylamine
FA—formic acid
Chemical Synthesis N-substituted peptidyl-α-ketoamides were synthesised in four stages using published methods:

(1) isocyanides corresponding to the tail modification were synthesised by Hoffman isocyanide synthesis from the corresponding primary amines (Cao et al., 2010), (2) the Boc-protected P1 amino acid was converted to an aminoaldehyde and then to the respective α-hydroxy-β-aminoamide by the Passerini reaction with the corresponding isocyanide (Semple et al., 2000, Venkatraman et al., 2006) as follows:

General Procedure for Coupling of Isocyanides to BOC-Protected Aminoaldehydes (Passerini Reaction):

Trifluoroacetic acid (2 eqv) was added dropwise to a cooled to −10° C. solution of BOC-Ala-CHO (1 eqv), isocyanide (1.2 eqv) and dry pyridine (4 eqv) in dry DCM under inert atmosphere. Then temperature was maintained at 0° C. for 2-3 h, after that ice bath was removed and the temperature was left to increase to an ambient one. The mixture was stirred 12-72 h at room temperature, according to TLC-control (hexane/ethylacetate=3:1). When BOC-Ala-CHO was depleted, the DCM was evaporated and the slurry was dissolved in ethylacetate. The mixture was washed with NaHCO$_3$ saturated aqueous solution (2×), 10% KHSO$_4$ (2×) and brine (1×). The ethylacetate layer was dried over MgSO$_4$, filtered off and evaporated, giving the crude product.

Trifluoroacetate ester was detected in most of the cases. It was removed by hydrolysis with 4 M NaOH added to a methanol solution of the crude product at r.t., according to HPLC control. Then methanol was evaporated and the residue was dissolved in ethylacetate and was washed with NaHCO$_3$ saturated aqueous solution (2×), 10% KHSO$_4$ (2×) and brine (1×). The ethylacetate layer was dried over MgSO$_4$, filtered off and evaporated, giving the crude product. The product can be purified by RP-HPLC chromatography, if necessary.

The following compounds were synthesised in steps (1) and (2):

Boc-NH—CH(CH$_3$)—CH(OH)—CONHBn, tert-butyl (4-(benzylamino)-3-hydroxy-4-oxobutan-2-yl) Carbamate LC-MS analysis: One peak at 9.27 min, corresponding to [M+Na$^+$] 331.16. Monoisotopic mass—desired product 308.17, calculated for C$_{16}$H$_{24}$N$_2$O$_4$.
$^1$H NMR (400 MHz, DMSO-d6) δ (ppm)=8.32 (d, J=27.4 Hz, 1H, CONH), 7.38-7.18 (m, 8H, CONH+Ar), 4.35-4.21 (m, 2H, CH$_2$), 3.88 (d, J=3.4 Hz, 1H), 3.81 (ddd, J=8.9, 6.6, 3.6 Hz, 1H), 3.75 (s, 1H, CH), 1.37 (s, 9H, BOC), 1.02 (d, J=6.7 Hz, 2H, CH$_3$), 0.86 (d, J=6.8 Hz, 1H, CH$_3$)— mixture of diastereomers.

Boc-NH—CH(CH$_3$)—CH(OH)CONHCH(CH$_3$)Ph, tert-butyl (3-hydroxy-4-oxo-4-((1-phenylethyl) amino)butan-2-yl)carbamate LC-MS analysis: One peak at 9.70 min, corresponding to [M+Na$^+$] 345.19. Monoisotopic mass: 322.19, calculated for C$_{17}$H$_{26}$N$_2$O$_4$.
$^1$H NMR (401 MHz, DMSO-d$_6$) δ (ppm)=8.14 (d, J=8.2 Hz, 1H, CONH), 7.37-7.24 (m, 4H, aromatic), 7.21 (q, J=6.6 Hz, 1H, aromatic), 6.14 (d, J=8.8 Hz, 1H, CONH), 4.93 (dq, J=14.8, 7.7, 7.1 Hz, 1H, CH), 3.84 (d, J=3.7 Hz, 1H, CH), 3.82-3.71 (m, 1H, CH), 1.43-1.30 (m, 12H, BOC, CH$_3$), 0.97 (d, J=6.6 Hz, 2H, CH$_3$), 0.90 (d, J=6.8 Hz, 1H, CH$_3$)— mixture of diastereomers.

Boc-NH—CH(CH$_3$)—CH(OH)CONHCy, tert-butyl (3-hydroxy-4-oxo-4-(cyclohexylamino) butan-2-yl) carbamate LC-MS analysis: One peak at 9.52 min, corresponding to the desired product [M+H$^+$] 301.2 and [M+Na$^+$] 323.19. Monoisotopic mass: 300.20, calculated for C$_{15}$H$_{28}$N$_2$O$_4$.
$^1$H NMR (401 MHz, DMSO-d$_6$) δ (ppm)=7.91 (s, 1H, CONH), 7.57-7.35 (m, 1H, CONH), 6.13 (d, J=8.6 Hz, 1H, CONH), 5.64-5.54 (m, 1H, CH), 3.77 (s, 1H, CH), 3.65-3.48 (m, 1H, CH), 1.66 (d, J=8.1 Hz, 5H, $CH_2$, aliphatic), 1.54 (d, J=12.6 Hz, 1H, $CH_2$, aliphatic), 1.35 (s, 9H, BOC), 1.31-1.20 (m, 4H, $CH_2$, aliphatic), 1.20-1.09 (m, 2H, $CH_2$, aliphatic), 1.00 (d, J=6.6 Hz, 2H, $CH_3$), 0.86 (d, J=6.8 Hz, 1H, $CH_3$)— mixture of diastereomers.

$^{13}C$ NMR (101 MHz, DMSO-$d_6$) δ (ppm)=171.04, 170.47, 159.90, 154.62, 77.63, 73.02, 48.89, 47.13, 46.02, 32.31, 32.01, 28.20, 25.14, 24.48, 17.14, 14.04.

Boc-NH—CH($CH_3$)—CH(OH)CONH$C_5H_{11}$, tert-butyl (3-hydroxy-4-oxo-4-(pentylamino) butan-2-yl) Carbamate The product was purified by preparative RP HPLC Gradient 15-50% B on 250×21 mm C18 column. LC-MS analysis: Single peak at 9.70 min, corresponding to the desired product [M+H$^+$] 289.2 and [M+Na$^+$] 311.19.

Boc-NH—CH($CH_3$)—CH(OH)CONH$CH_2CH_2$Ph, tert-butyl (3-hydroxy-4-oxo-4-((2-phenylethyl)amino)butan-2-yl)carbamate LC-MS analysis: One peak at 9.72 min, corresponding to [M+Na$^+$] 345.11. Monoisotopic mass: 322.19, calculated for $C_{17}H_{26}N_2O_4$.

Boc-NH—CH($CH_3$)—CH(OH)CONH$CH_2C_6H_3$(2,5-$CH_3$)$_2$, tert-butyl [4-((2,5-dimethyl) benzylamino)-3-hydroxy-4-oxobutan-2-yl) Carbamate The desired product appears as a major peak at 10.29 min. [M+H$^+$] 337.21 and [M+Na$^+$] 359.2). No trifluoroacetate ester was detected. Monoisotopic mass: 336.20, calculated for $C_{18}H_{28}N_2O_4$.

Boc-NH—CH($CH_3$)—CH(OH)CONH$CH_2$COOEt, ethyl 2-(3-((tert-butoxycarbonyl)amino)-2-hydroxybutanamido)acetate The product was purified by preparative RP-HPLC, using gradient 15-50% B on 250×21 mm C18 column.

LC-MS analysis: The product elutes as a one peak at 8.36 min, corresponding to [M+Na$^+$] 327.2 Monoisotopic mass: 304.16, calculated for $C_{13}H_{24}N_2O_6$.

Boc-NH—CH($CH_3$)—CH(OH)CONH$CH_2$C($CH_3$)$_3$, tert-butyl (3-hydroxy-4-oxo-4-(neopentylamino)butan-2-yl) Carbamate LC-MS analysis: One peak which was eluting at 9.39 min, corresponding to the desired product [M+H$^+$] 289.2 and [M+Na$^+$] 311.19. Monoisotopic mass: 288.20, calculated for $C_{14}H_{28}N_2O_4$.

Boc-NH—CH($CH_3$)—CH(OH)CONH($CH_2$)$_4$Ph, tert-butyl (3-hydroxy-4-oxo-4-(4-phenylbutylamino)butan-2-yl) Carbamate LC-MS analysis: One peak, eluting at 10.4 min, corresponding to the desired product [M+H$^+$] 351.2 and [M+Na$^+$] 373.2. Monoisotopic mass: 350.22 calculated for $C_{19}H_{30}N_2O_4$.

Boc-NH—CH($CH_3$)—CH(OH)CONHCH($CH_3$)$_2$ tert-butyl (3-hydroxy-4-oxo-4-(4-isopropylamino) butan-2-yl) Carbamate LC-MS analysis: Single peak at 8.31 min, corresponding to the desired product [M+H$^+$] 261.18 and [M+Na$^+$] 283.16. Monoisotopic mass: 260.17, calculated for $C_{12}H_{24}N_2O_4$.

(3) The peptide component corresponding to the P5 to P2 segment of the inhibitor was synthesised on solid phase using the 2-chlorotrityl resin, and (4) the deprotected α-hydroxy-β-aminoamide hydrochloride was coupled to the P5-P2 peptide (Coste et al, J Org Chem, 1994) as detailed below:

General Procedure for the Coupling of H-Ala-CH(OH)—CONHX. HCl (X=Bn, Cy, CH($CH_3$)Ph, $C_5H_{11}$) to Ac-Arg(Pbf)-Val-Arg(Pbf)-His(Trt)-OH The protected peptide (1 eqv) has been activated in DMF solution (0.8 ml) by the consequent addition of TCFH (1.2 eqv) and DIEA (1.7 eqv) 2-3 min prior to the coupling. Then $H_2N$—CH($CH_3$)—CH(OH)—CONHX. HCl have been added (2 eqv) as a solution in 0.5 ml DMF. DIEA (1.6 eqv) was added at the end. The mixture was stirred overnight at room temperature. pH of the reaction mixture must be basic. The DMF was evaporated and the oil-like product was triturated with 10% $KHSO_4$ till the pale-yellow precipitate was formed. It was washed on a sintered glass with 10% $KHSO_4$ and water. The product was dried in vacuo. The following products were synthesized:

Ac-Arg(Pbf)-Val-Arg(Pbf)-His(Trt)-NH—CH($CH_3$)—CH(OH)—CONHBn

LC-MS analysis: One peak at 8.94 min with the molecular mass [M+Na$^+$] 1567.73 and [M−Trt+H$^+$] 1303.63 and 9.03 min [M+H$^+$] 1545.74 and [M−Trt+H]$^+$ 1303.63 (diastereomers). Monoisotopic mass: 1544.73, calculated for $C_{81}H_{104}N_{14}O_{13}S_2$.

Ac-Arg(Pbf)-Val-Arg(Pbf)-His(Trt)-NH—CH($CH_3$)—CH(OH)—CONHCH($CH_3$)Ph

LC-MS analysis: Two peaks at 7.92, 8.0 min with the mass, corresponding to the product [M−Trt+H$^+$] 1317.64 and other two at 8.9 and 9.0 min with masses [M−Trt+H$^+$] 1317.64 and [M+H$^+$] 1559.75. Monoisotopic mass: 1558.75, calculated for $C_{82}H_{106}N_{14}O_{13}S_2$.

Ac-Arg(Pbf)-Val-Arg(Pbf)-His(Trt)-NH—CH($CH_3$)—CH(OH)—CONHCy

LC-MS analysis: There are two peaks 11.84 and 11.95 min, corresponding to a desired product with [M+H$^+$] 1537.77 (diastereomeric couple). Monoisotopic mass: 1536.77, calculated for $C_{80}H_{108}N_{14}O_{13}S_2$.

Ac-Arg(Pbf)-Val-Arg(Pbf)-His(Trt)-NH—CH($CH_3$)—CH(OH)—CONH$C_5H_{11}$

LC-MS analysis: Three double peaks at 11.59, 11.69 and 11.79 min, corresponding to the product [M+H$^+$] 1525.77. Monoisotopic mass: 1524.77, calculated for $C_{79}H_{108}N_{14}O_{13}S_2$.

General Procedure for the Coupling of H-Ala-CH(OH)—CONHX. HCl (X=—($CH_2$)$_2$Ph, —($CH_2$)$_4$Ph, —$CH_2C_6H_3$(2,5-dimethyl, —$CH_2$COOEt, —CH($CH_3$)$_2$, —$CH_2$C($CH_3$)$_3$)) to Ac-Arg(Pbf)-Val-Arg(Pbf)-His(Trt)-OH.

The protected peptide (1 eqv), PyBrOP (1.5 eqv) and HOBt (1-1.5 eqv) have been dissolved in DCM (0.8 ml) and cooled to 0° C. Then the solution of H$_2$N—CH(CH$_3$)—CH(OH)—CONHX. HCl in DCM (0.4 ml), neutralized by micropipette titration with DIEA and poured into the reaction flask, followed by the addition of 3 eqv. DIEA. The reaction mixture was left to stir at 0° C. for 1-2 min, then the ice bath was removed and the stirring continues at ambient temperature as long as it was needed (HPLC—control 2-100% B). When the starting compounds have been depleted, the reaction mixture was diluted with EtOAc (40×), washed with aq.NaHCO$_3$ (2×), 10% KHSO$_4$ (2×) and water (1×). The combined ethylacetate layers were dried over MgSO$_4$, filtered off and evaporated, giving the crude product.

Ac-Arg(Pbf)-Val-Arg(Pbf)-His(Trt)-NH—CH(CH$_3$)—CH(OH)—CONH(CH$_2$)$_2$Ph

LC-MS analysis: Two peaks at 11.63 and 11.73 min, corresponding to the mass of the desired product: M$_{mi}$+H$^+$ 1559.75 (mixture of diastereomers). Monoisotopic mass: 1558.75, calculated for C$_{82}$H$_{106}$N$_{14}$O$_{13}$S$_2$.

Ac-Arg(Pbf)-Val-Arg(Pbf)-His(Trt)-NH—CH(CH$_3$)—CH(OH)—CONHCH$_2$Ph(2,5-dimethyl)

LC-MS analysis: Two peaks at 11.77 and 11.93 min, corresponding to the mass of the desired product: [M+H$^+$] 1573.76 (mixture of diastereomers). Monoisotopic mass: 1572.77, calculated for C$_{83}$H$_{108}$N$_{14}$O$_{13}$S$_2$.

Ac-Arg(Pbf)-Val-Arg(Pbf)-His(Trt)-NH—CH(CH$_3$)—CH(OH)—CONHCH$_2$COOEt

LC-MS analysis: Two peaks at 11.12 and 11.17 min, corresponding to the mass of the desired product [M+H$^+$] 1541.72 (mixture of diastereomers). Monoisotopic mass: 1540.72, calculated for C$_{78}$H$_{104}$N$_{14}$O$_{15}$S$_2$.

Ac-Arg(Pbf)-Val-Arg(Pbf)-His(Trt)-NH—CH(CH$_3$)—CH(OH)—CONHCH$_2$C(CH$_3$)$_3$

LC-MS analysis: Two peaks at 11.39 and 11.47 min, corresponding to the mass of the desired product: [M+H$^+$] 1525.75 (mixture of diastereomers). Monoisotopic mass: 1524.77, calculated for C$_{79}$H$_{108}$N$_{14}$O$_{13}$S$_2$.

Ac-NH—CH(CH$_3$)—CH(OH)—CONH(CH$_2$)$_2$Ph

LC-MS analysis: Two peaks at 7.17 and 7.43 min, corresponding to the same molecular mass [M+H]$^+$ 265.16 (diastereomers). Monoisotopic mass: 264.15, calculated for C$_{14}$H$_{20}$N$_2$O$_3$.

These compounds were oxidised by the Dess-Martin oxidation, as detailed below.

General Procedure for Oxidation of Peptidyl-α-Hydroxyamides to Peptidyl-α-Ketoamides by Dess-Martin Oxidation (Souček et al., 1995).

The solution of peptidyl-α-hydroxyamide (1 eqv) in 0.6 ml dry DCM was poured to a solution of Dess-Martin periodinane (1.25 eqv) in 1 ml dry DCM, containing tBuOH (1.1 eqv). The reaction mixture was stirred under inert atmosphere at room temperature, according to the HPLC control. When the starting compound was depleted, the periodinane was destroyed by the addition of sat. NaHCO$_3$ and 1M Na$_2$S$_2$O$_3$ and stirring intensively for 20 min. The mixture was diluted with DCM and DCM layer was separated and dried over MgSO$_4$. Filtration of the drying agent and evaporation of the solvent are giving the crude product.

Ac-Arg(Pbf)-Val-Arg(Pbf)-His(Trt)-NH—CH(CH$_3$)—CO—CONHBn

LC-MS analysis: Three peaks at 9.02, 9.19 and 9.28 min, corresponding to the desired mass [M+Na$^+$] 1566.78 and mass [M+H$^+$] 1543.72. Monoisotopic mass: 1542.72, calculated for C$_{81}$H$_{102}$N$_{14}$O$_{13}$S$_2$.

Ac-Arg(Pbf)-Val-Arg(Pbf)-His(Trt)-NH—CH(CH$_3$)—CO—CONHCH(CH$_3$)Ph

LC-MS analysis: Two peaks at 11.94 and 12.08 min, corresponding to the desired mass [M−Trt+H$^+$] 1315.63. Monoisotopic mass: 1556.73, calculated for C$_{82}$H$_{104}$N$_{14}$O$_{13}$S$_2$.

Ac-Arg(Pbf)-Val-Arg(Pbf)-His(Trt)-NH—CH(CH$_3$)—CO—CONHCy

LC-MS analysis: Three peaks at 11.88, 12.10 and 12.25 min, corresponding to the desired mass [M+H$^+$] 1535.75. Monoisotopic mass: 1534.75, calculated for C$_{80}$H$_{106}$N$_{14}$O$_{13}$S$_2$.

Ac-Arg(Pbf)-Val-Arg(Pbf)-His(Trt)-NH—CH(CH$_3$)—CO—CONHC$_5$H$_{11}$

LC-MS analysis: One peak at 9.22 min, corresponding to the desired mass [M+H$^+$] 1523.75. Monoisotopic mass: 1522.75, calculated for C$_{79}$H$_{106}$N$_{14}$O$_{13}$S$_2$.

Ac-Arg(Pbf)-Val-Arg(Pbf)-His(Trt)-NH—CH(CH$_3$)—CO—CONH(CH$_2$)$_2$Ph

LC-MS analysis: Two peaks at 11.94 and 12.04 min, corresponding to the desired mass [M+H$^+$] 1557.74. Monoisotopic mass: 1556.73, calculated for C$_{82}$H$_{104}$N$_{14}$O$_{13}$S$_2$.

Ac-Arg(Pbf)-Val-Arg(Pbf)-His(Trt)-NH—CH(CH$_3$)—CO—CONHCH$_2$COOEt

LC-MS analysis: Two peaks at 11.30 and 11.52 min, corresponding to the desired mass [M+H$^+$] 1539.71. Monoisotopic mass: 1538.71, calculated for C$_{78}$H$_{102}$N$_{14}$O$_{15}$S$_2$.

Ac-Arg(Pbf)-Val-Arg(Pbf)-His(Trt)-NH—CH(CH$_3$)—CO—CONH(CH$_2$)$_4$Ph

LC-MS analysis: One broad peak at 11.5 min, corresponding to the desired mass [M+H$^+$] 1586.77. Monoisotopic mass: 1584.77, calculated for C$_{84}$H$_{108}$N$_{14}$O$_{13}$S$_2$.

Ac-Arg(Pbf)-Val-Arg(Pbf)-His(Trt)-NH—CH(CH$_3$)—CO—CONHCH$_2$C(CH$_3$)$_3$

LC-MS analysis: One broad peak at 11.3 min, corresponding to the desired mass [M+H$^+$] 1523.75. Monoisotopic mass: 1522.75, calculated for C$_{79}$H$_{106}$N$_{14}$O$_{13}$S$_2$.

Ac-His(Trt)-NH—CH(CH$_3$)—CO—CONH(CH$_2$)$_2$Ph

LC-MS analysis: One broad peak at 9.4 min, corresponding to the desired mass [M+H$^+$] 642.31. Monoisotopic mass: 641.30, calculated for C$_{39}$H$_{39}$N$_{15}$O$_4$.

General Procedure for Swern Oxidation of Ac-Arg(Pbf)His(Trt)-NHCH(CH$_3$)—CH(OH)CONH— Phenylethyl (Yin et al., 2007)

Dry flask was charged with 0.5 ml dry DCM and was cooled down to −78° C. (dry ice/acetone). Oxalyl chloride (0.15 mmol, 13 µl) and DMSO (0.2 mmol, 14.2 µl) were subsequently added to the cooled DCM and the solution was stirred for 15-20 min. Then Ac-Arg(Pbf)His(Trt)-NH—CH(CH$_3$)—CH(OH)CONH— phenylethyl (53 mg, 0.05 mmol) in 0.5-0.6 ml dry DCM was added and the mixture was stirred for 2 h at −78° C. The reaction was quenched by pouring of Et$_3$N (0.3 mmol, 42 µl), the mixture was warmed to a room temperature over 30 min. The mixture was treated with 1 ml of water, followed by 10 min stirring. Extractions of the water layer were made by 6-7 ml DCM (2×). DCM layer was washed with 10% KHSO$_4$ (2×), brine (1×) and dried over MgSO$_4$. DCM was evaporated, giving the crude product.

The unsubstituted ketoamide has been synthesized by transforming the aldehyde moiety of the Boc-protected P1 aminoaldehyde formed in step (2) to a cyanhydrin and subsequent partial hydrolysis of the cyanide moiety to an amide (Venkatraman et al., 2006).

HPLC analyses were performed, using gradients from phase A (water+0.1% TFA) to phase B (acetonitrile) on Watrex C18 column 250×4.6 mm.

LC-MS: Gradient: 2% B to 100% B over 10 min was used on a Waters 1.7 am C18, 100×2.1 column at a flow rate 0.3 ml/min, where A: 0.1% FA/water and B: 0.1% FA/ACN).

The orthogonal protection groups were removed to yield the final N-substituted peptidyl-α-ketoamides summarised Example 1 to 15.

The amino acid sequences in compounds 1-15 correspond to SEQ ID NO. 1 and to SEQ ID NO. 2.

Example 1

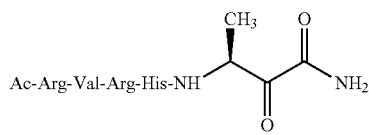

Compound 1

LC-MS analysis: Gradient 2-30% B over 7 min; Three diastereomeric peaks at 1.85, 2.03 and 2.2 min, corresponding to [M+H]$^+$ 707.4.

HR-MS: Monoisotopic mass: 706.40, calculated for C$_{29}$H$_{50}$N$_{14}$O$_7$; found [M+H]$^+$ 707.40638 and [M+2H]$^{2+}$ 354.20689.

Example 2

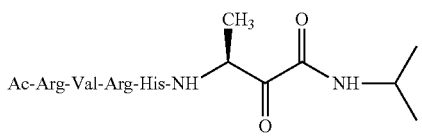

Compound 2

HPLC analysis: Gradient 2-100% B over 36 min.; One peak at 13.45 min.

ESI-MS: [M+H]$^+$ 749.6, [M+Na]$^+$ 771.6, [M+2H]$^{2+}$ 375.3.

HR-MS: Monoisotopic mass: 748.45, calculated for C$_{32}$H$_{56}$N$_{14}$O$_7$; found [M+H]$^+$ 749.45324, [M+Na]$^+$ 771.43518 and [M+2H]$^{2+}$ 375.23028.

$^1$H NMR (401 MHz, DMSO-d$_6$) δ (ppm)=8.93 (s, 1H, COCONH), 8.53 (d, J=8.3 Hz, 1H, aromatic), 8.43 (d, J=6.3 Hz, 1H, CONH), 8.25 (d, J=7.9 Hz, 1H, CONH), 8.21-8.11 (m, 2H, CONH), 7.74-7.58 (m, 3H, CONH+NH$_2$), 7.33 (s, 1H, aromatic), 5.13-4.93 (m, 1H, CH), 4.69-4.56 (m, 1H, CH), 4.36-4.13 (m, 3H, CH), 3.93 (dt, J=14.8, 7.3 Hz, 1H, CH), 3.09 (d, J=5.6 Hz, 5H, CH+CH$_2$), 3.00-2.85 (m, 1H, CH), 1.97 (dd, J=15.0, 8.3 Hz, 1H, CH), 1.88 (s, 3H, COCH$_3$), 1.73-1.58 (m, 2H, CH$_2$), 1.49 (dt, J=15.2, 9.0 Hz, 6H, CH$_2$), 1.26 (d, J=7.3 Hz, 3H, CH$_3$), 1.11 (d, J=6.6 Hz, 6H, CH$_3$), 0.80 (dd, J=11.5, 6.7 Hz, 6H, CH$_3$).

$^{13}$C NMR (101 MHz, DMSO-d$_6$) δ (ppm)=187.06, 171.49, 171.27, 159.60, 156.72, 135.61, 133.76, 115.70, 104.52, 57.14, 52.38, 49.54, 30.78, 28.71, 25.07, 22.46, 21.79, 19.10, 17.88, 15.61.

Example 3

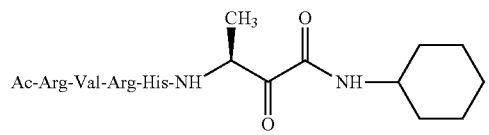

Compound 3

LC-MS analysis: One peak at 5.87 min with the corresponding mass of the product [M+H]$^+$ 789.48.

HR-MS: Monoisotopic mass: 788.4769 calculated for C$_{35}$H$_{60}$N$_{14}$O$_7$ found: [M+2H]$^{2+}$ 395.24606 and [M+3H]$^{3+}$ 263.83329.

$^1$H NMR (401 MHz, DMSO-d$_6$) δ (ppm)=14.30 (s, 2H, NH), 9.03-8.93 (m, 1H, CONH), 8.55-8.47 (m, 1H, aromatic), 8.42 (t, J=6.4 Hz, 1H, CONH), 8.25 (d, J=8.1 Hz, 1H, CONH), 8.16 (q, J=6.7 Hz, 2H, CONH), 7.64 (dtd, J=14.0, 8.7, 4.9 Hz, 3H, CONH), 7.39-7.31 (m, 1H, aromatic), 5.02 (tt, J=9.7, 5.8 Hz, 1H, CH), 4.62 (td, J=8.1, 5.6 Hz, 1H, CH), 4.31-4.22 (m, 1H, CH), 4.19 (dtd, J=11.2, 6.2, 2.9 Hz, 2H, CH), 3.57 (dt, J=19.8, 6.2 Hz, 1H, CH), 3.07 (q, J=6.4 Hz, 5H, CH$_2$), 2.96-2.83 (m, 1H, CH$_2$ His), 2.02-1.89 (m, 1H, CH), 1.87 (d, J=2.2 Hz, 3H, acetyl), 1.74-1.58 (m, 6H, CH$_2$), 1.49 (dtd, J=25.9, 15.5, 14.7, 6.3 Hz, 7H, CH$_2$), 1.26 (dq, J=14.3, 11.4, 10.8 Hz, 7H), 0.79 (dd, J=11.4, 6.8 Hz, 6H, CH$_3$).

$^{13}$C NMR (101 MHz, DMSO-d$_6$) δ (ppm)=171.49, 171.28, 169.62, 158.58, 158.26, 156.73, 133.72, 129.06, 115.37, 57.16, 52.40, 49.59, 48.07, 31.78, 30.78, 28.75, 25.07, 24.73, 22.46, 19.10, 17.89, 15.60.

Example 4

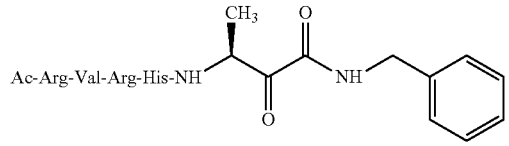

Compound 4

LC-MS analysis: One peak at 6.07 min with the corresponding mass of the product [M+H]$^+$ 797.45.

HR-MS: Monoisotopic mass: 796.4456 calculated for $C_{36}H_{56}N_{14}O_7$ found: [M+H]$^+$ 797.45282.

Yield: 1.3 mg (4.2%).

Example 5

Ac—Arg—Val—Arg—His—NH—C(CH$_3$)H—C(O)—NH—C(CH$_3$)H—Ph

Compound 5

HPLC analysis: One peak at 14.2 min Gradient 2-100% B over 36 min. ESI-MS: [M+H]$^+$ 811.5.

HR-MS: Monoisotopic mass: 810.46129, calculated for $C_{37}H_{58}N_{14}O_7$ found: [M+H]$^+$ 811.46909 and [M+2H]$^{2+}$ 406.23814.

$^1$H NMR (401 MHz, DMSO-d$_6$) δ (ppm)=14.30 (s, 1H, NH), 9.23-9.10 (m, 1H, CONH), 8.97 (s, 1H, aromatic), 8.45 (dd, J=14.2, 6.5 Hz, 1H, CONH), 8.19 (dd, J=31.1, 7.9 Hz, 3H, CONH), 7.61 (s, 3H), 7.34 (dt, J=9.9, 4.3 Hz, 6H, Ar), 7.28-7.20 (m, 1H, CONH), 4.98 (dt, J=15.2, 7.5 Hz, 2H, CH), 4.61 (q, J=7.8 Hz, 1H, CH), 4.22 (dq, J=33.3, 7.4, 5.5 Hz, 3H, CH), 3.18-2.98 (m, 5H, CH$_2$), 2.87 (dd, J=15.7, 8.2 Hz, 1H, CH$_2$), 1.93 (dd, J=12.7, 6.0 Hz, 1H, CH), 1.87 (s, 3H, acetyl), 1.72-1.58 (m, 2H, CH$_2$), 1.43 (td, J=25.5, 22.6, 8.5 Hz, 9H, CH$_2$, CH$_3$), 1.27 (d, J=7.3 Hz, 2H, CH$_2$), 1.16 (d, J=7.1 Hz, 1H, CH$_3$), 0.79 (dt, J=10.9, 5.7 Hz, 6H, CH$_3$).

$^{13}$C NMR (101 MHz, DMSO-d$_6$) δ (ppm)=198.27, 173.20, 171.62, 169.73, 156.75, 139.20, 128.31, 126.18, 104.52, 67.45, 59.85, 52.41, 51.24, 48.24, 47.47, 28.75, 25.13, 22.46, 21.70, 19.09, 17.87, 15.54.

Example 6

Ac—Arg—Val—Arg—His—NH—C(CH$_3$)H—C(O)—NH—CH$_2$—C(O)—O—CH$_2$CH$_3$

Compound 6

HPLC analysis: Gradient 2-30% B over 30 min; One peak at 12.4 min.

ESI-MS: [M+H]$^+$ 792.4, [M+2H]$^{2+}$ 397.2.

HR-MS: Monoisotopic mass: 792.43552, calculated for $C_{33}H_{56}N_{14}O_9$; found: [M+H]$^+$ 793.44299, [M+2H]$^{2+}$ 397.22539.

$^1$H NMR (401 MHz, DMSO-d$_6$) δ (ppm)=14.17 (s, 1H, NH imidazole), 9.03 (t, J=5.9 Hz, 1H, CONH), 8.45 (d, J=6.3 Hz, 1H, aromatic), 8.26 (d, J=7.5 Hz, 1H, CONH), 8.15 (d, J=7.8 Hz, 2H, CONH), 7.58 (t, J=9.1 Hz, 2H, CONH), 7.37-7.26 (m, 1H, aromatic), 5.01 (p, J=6.4, 5.8 Hz, 1H, CH), 4.61 (q, J=8.0 Hz, 1H, CH), 4.35-4.05 (m, 5H, CH+CH$_2$), 3.90 (d, J=6.8 Hz, 2H, CH$_2$), 3.19-2.97 (m, 5H, CH$_2$), 2.91 (dd, J=15.2, 8.0 Hz, 1H, CH$_2$), 1.98-1.90 (m, 1H, CH), 1.87 (s, 3H, acetyl), 1.74-1.58 (m, 2H, CH$_2$), 1.49 (dq, J=16.1, 7.7 Hz, 6H, CH$_2$), 1.31-1.12 (m, 6H, CH$_3$), 0.79 (dd, J=11.9, 6.7 Hz, 6H, CH$_3$).

$^{13}$C NMR (101 MHz, DMSO-d$_6$) δ (ppm)=168.83, 166.37, 164.30, 162.00, 156.67, 146.64, 139.66, 135.98, 134.39, 123.99, 60.73, 57.15, 53.86, 52.36, 49.54, 45.52, 28.75, 22.47, 21.18, 19.10, 14.05.

Example 7

Ac—Arg—Val—Arg—His—NH—C(CH$_3$)H—C(O)—NH—CH$_2$C(CH$_3$)$_3$

Compound 7

LC-MS analysis: One peak at 5.66 min, corresponding to [M+H]$^+$ 777.5, [M+2H]$^{2+}$ 389.3, [M+3H]$^{3+}$ 259.85.

HR-MS: Monoisotopic mass: 776.476941, calculated for $C_{34}H_{60}N_{14}O_7$; found [M+H]$^+$ 777.48454, [M+Na]$^+$ 799.46650 and [M+2H]$^{2+}$ 389.24594.

$^1$H NMR (401 MHz, DMSO-d$_6$) δ (ppm)=14.29 (s, 1H, NH imidazole), 8.94 (s, 1H, COCONH), 8.57 (s, 1H, aromatic), 8.42 (d, J=6.4 Hz, 1H, CONH), 8.25 (d, J=8.1 Hz, 1H, CONH), 8.15 (t, J=7.4 Hz, 2H, CONH), 7.64 (dd, J=21.6, 10.8 Hz, 2H, CONH+NH), 7.33 (s, 1H, aromatic), 5.12-4.94 (m, 1H, CH), 4.68-4.56 (m, 1H, CH), 4.35-4.12 (m, 3H, CH), 3.18-3.00 (m, 5H, CH$_2$), 2.96 (d, J=6.8 Hz, 3H, CH$_2$), 2.03-1.90 (m, 1H, CH), 1.87 (s, 3H, COCH$_3$), 1.65 (dt, J=16.3, 8.0 Hz, 2H, CH$_2$), 1.47 (dq, J=24.5, 12.2, 10.4 Hz, 6H, CH$_2$), 1.23 (dd, J=17.4, 7.3 Hz, 3H, CH$_3$), 0.94-0.63 (m, 15H, CH$_3$).

$^{13}$C NMR (101 MHz, DMSO-d$_6$) δ (ppm)=196.92, 171.82, 171.51, 169.70, 161.17, 158.66, 156.75, 133.76, 57.16, 52.42, 51.05, 49.54, 32.62, 30.76, 28.75, 27.32, 25.14, 22.46, 19.10, 17.88, 15.46.

Example 8

Ac—Arg—Val—Arg—His—NH—C(CH$_3$)H—C(O)—NH—(CH$_2$)$_4$CH$_3$

Compound 8

HPLC analysis: One peak at 14.34 min, Gradient 2-100% B over 36 min.

ESI-MS: [M+H]$^+$ 777.5, [M+Na]$^+$ 799.5.

HR-MS: Monoisotopic mass: 776.476941, calculated for $C_{34}H_{60}N_{14}O_7$; found: [M+H]$^+$ 777.48440, [M+2H]$^{2+}$ 389.24586.

$^1$H NMR (401 MHz, DMSO-d$_6$) δ (ppm)=14.20 (s, 1H, NH imidazole), 8.91 (s, 1H, CONH), 8.68 (t, J=5.8 Hz, 1H, CONH), 8.41 (d, J=6.4 Hz, 1H, aromatic), 8.20 (dd, J=35.0, 7.4 Hz, 3H, CONH), 7.61 (d, J=6.4 Hz, 3H, CONH+NH$_2$), 7.32 (s, 2H, NH$_2$), 5.02 (p, J=7.2 Hz, 1H, CH), 4.61 (q, J=7.8, 7.0 Hz, 1H, CH), 4.22 (dt, J=31.2, 7.7 Hz, 3H, CH), 3.09 (dq, J=12.1, 6.9 Hz, 7H, CH$_2$), 2.98-2.82 (m, 1H, CH$_2$), 2.18-2.03 (m, 1H, CH), 1.87 (s, 3H, acetyl), 1.64 (td, J=14.1, 12.8, 7.1 Hz, 2H, CH$_2$), 1.58-1.34 (m, 8H, CH$_2$), 1.23 (tt, J=15.5, 7.3 Hz, 7H, CH$_2$+CH$_3$), 0.93-0.67 (m, 9H, CH$_3$).

Example 9

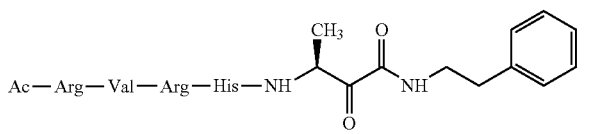

Compound 9

HPLC analysis: Gradient 2-30% B over 30 min; One peak at 22.2 min. ESI-MS: [M+H]$^+$ 811.3, [M+2H]$^{2+}$ 406.2

HR-MS: Monoisotopic mass 810.461290, calculated for $C_{32}H_{58}N_{14}O_2$; found: [M+H]$^+$ 811.46886, [M+2H]$^{2+}$ 406.23800.

$^1$H NMR (401 MHz, DMSO-d$_6$) δ (ppm)=14.20 (s, 1H, NH imidazole), 8.93 (s, 1H, NH), 8.77 (t, J=5.9 Hz, 1H, CONH), 8.41 (d, J=6.2 Hz, 1H, aromatic), 8.25 (d, J=7.9 Hz, 1H, CONH), 8.15 (t, J=7.4 Hz, 2H, CONH), 7.62 (t, J=10.9 Hz, 3H, CONH), 7.30 (dd, J=14.5, 6.8 Hz, 5H, aromatic), 7.20 (d, J=7.6 Hz, 5H, aromatic+NH$_2$), 5.01 (p, J=7.2 Hz, 1H, CH), 4.62 (q, J=8.0 Hz, 1H, CH), 4.34-4.12 (m, 3H, CH), 3.16-2.99 (m, 5H, CH$_2$), 2.91 (dd, J=15.3, 8.1 Hz, 1H, CH$_2$), 2.77 (t, J=7.5 Hz, 2H, CH$_2$), 2.00-1.90 (m, 1H, CH), 1.87 (s, 3H, acetyl), 1.73-1.57 (m, 2H, CH$_2$), 1.48 (dt, J=19.0, 11.3 Hz, 6H, CH$_2$), 1.20 (d, J=7.3 Hz, 3H, CH$_3$), 0.79 (dd, J=11.0, 6.8 Hz, 6H, CH$_3$).

$^{13}$C NMR (101 MHz, DMSO-d$_6$) δ (ppm)=196.62, 171.49, 171.28, 169.69, 169.59, 160.23, 158.33, 156.73, 138.95, 133.74, 128.60, 128.35, 126.21, 118.66, 57.16, 55.97, 52.41, 51.05, 49.45, 40.41, 34.57, 30.78, 28.74, 25.14, 22.47, 19.11, 17.89, 15.50.

Example 10

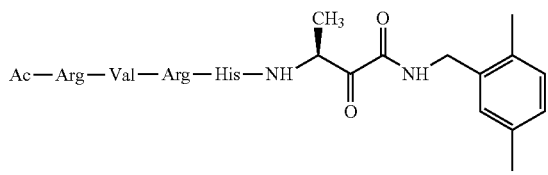

Compound 10

HPLC analysis: One peak at 6.35 min, corresponding to [M+H]$^+$ 825.5, [M+2H]$^{2+}$ 413.3, [M+3H]$^{3+}$ 275.84.

HR-MS: Monoisotopic mass: 824.47694, calculated for $C_{38}H_{60}N_{14}O_7$ found: [M+H]$^+$ 825.48462, [M+2H]$^{2+}$ 413.24584.

$^1$H NMR (401 MHz, DMSO-d$_6$) δ (ppm)=14.25 (s, 1H, NH imidazole), 9.09 (t, J=6.0 Hz, 1H, CONH), 8.95 (s, 1H, NH), 8.45 (d, J=6.3 Hz, 1H, aromatic), 8.25 (d, J=8.1 Hz, 1H, CONH), 8.15 (t, J=6.7 Hz, 2H, CONH), 7.62 (dt, J=13.8, 6.6 Hz, 2H, CONH), 7.33 (s, 1H, aromatic), 7.10-6.89 (m, 3H, aromatic), 5.04 (p, J=7.2 Hz, 1H, CH), 4.61 (q, J=7.9 Hz, 1H, CH), 4.33-4.11 (m, 5H, CH+CH$_2$), 3.16-3.00 (m, 5H, CH$_2$), 2.90 (dd, J=15.1, 7.9 Hz, 1H, CH$_2$), 2.22 (s, 6H, CH$_3$), 1.95 (dt, J=13.3, 8.1 Hz, 1H, CH), 1.87 (s, 3H, acetyl), 1.72-1.58 (m, 2H, CH$_2$), 1.57-1.33 (m, 6H, CH$_2$), 1.27 (d, J=7.3 Hz, 3H, CH$_3$), 0.79 (dd, J=11.1, 6.8 Hz, 6H, CH$_3$).

$^{13}$C NMR (101 MHz, DMSO-d$_6$) δ (ppm)=200.01, 171.50, 171.30, 170.98, 169.70, 165.73, 160.58, 158.48, 156.72, 135.75, 134.51, 133.74, 129.93, 128.40, 127.59, 57.15, 52.41, 51.06, 49.58, 30.77, 28.71, 25.06, 22.46, 20.68, 19.10, 18.08, 15.53.

Example 11

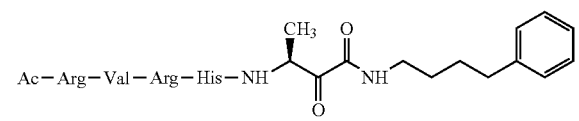

Compound 11

HPLC analysis: Gradient 2-100% B over 36 min; One peak at 16.0 min.

ESI-MS: [M+H]$^+$ 839.5, [M+2H]$^{2+}$ 420.3.

HR-MS: Monoisotopic mass: 838.49263 calculated for $C_{39}H_{62}N_{14}O_7$; found [M+H]$^+$ 839.5007, [M+2H]$^{2+}$ 420.25366.

$^1$H NMR (401 MHz, DMSO-d$_6$) δ (ppm)=14.17 (s, 1H, NH imidazole), 8.88 (s, 1H, COCONH), 8.71 (t, J=5.8 Hz, 1H, aromatic), 8.41 (d, J=6.4 Hz, 1H, CONH), 8.24 (d, J=7.8 Hz, 1H, aromatic, CONH), 8.15 (d, J=7.6 Hz, 2H, CONH), 7.59 (d, J=6.2 Hz, 3H CONH), 7.27 (dd, J=14.8, 7.1 Hz, 4H, aromatic), 7.18 (d, J=7.9 Hz, 3H, aromatic), 5.08-4.95 (m, 1H, CH), 4.61 (q, J=8.2, 7.0 Hz, 1H, CH), 4.22 (dt, J=30.8, 8.0 Hz, 3H, CH), 3.11 (dd, J=28.1, 6.1 Hz, 7H, CH$_2$), 2.99-2.84 (m, 1H, CH$_2$), 2.56 (d, J=7.5 Hz, 3H, CH$_2$), 2.00-1.89 (m, 1H, CH), 1.87 (s, 3H, COCH$_3$), 1.75-1.33 (m, 12H, CH$_2$), 1.21 (dd, J=18.8, 7.3 Hz, 3H, CH$_3$), 0.79 (dd, J=11.5, 6.8 Hz, 6H, CH$_3$).

$^{13}$C NMR (101 MHz, DMSO-d$_6$) δ (ppm)=207.16, 187.80, 169.69, 160.34, 156.70, 142.01, 128.27, 125.68, 71.09, 69.06, 57.12, 52.39, 44.45, 34.68, 28.29, 25.05, 22.46, 19.12, 17.87.

Example 12

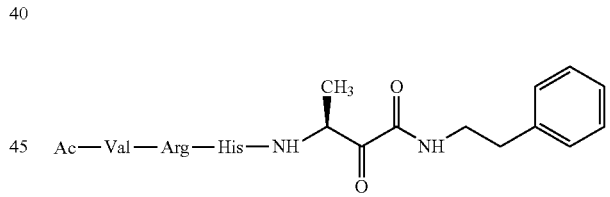

Compound 12

LC-MS analysis: One peak at 5.70 min, corresponding to [M+H]$^+$ 655.37 and [M+2H]$^{2+}$ 328.19.

HR-MS: Monoisotopic mass: 654.360179 calculated for $C_{31}H_{46}N_{10}O_6$, found [M+H]$^+$ 655.36774 and [M+Na]$^+$ 677.34979.

Yield: 1.5 mg (14%).

Example 13

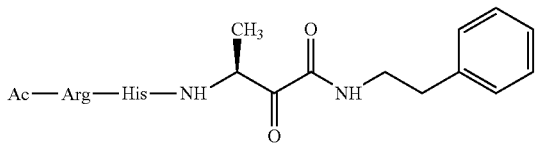

Compound 13

LC-MS analysis: One peak at 5.97 min, corresponding to [M+H]$^+$ 556.30 and [M+2H]$^{2+}$ 278.65.

HR-MS: Monoisotopic mass: 555.291765 calculated for $C_{26}H_{37}N_9O_5$, found [M+H]$^+$ 556.29939.

$^1$H NMR (401 MHz, DMSO-d$_6$) δ (ppm)=14.14 (s, 2H, NH imidazole), 8.95 (s, 1H, aromatic), 8.77 (t, J=4.7 Hz, 1H, COCONH), 8.38-8.08 (m, 3H, CONH), 7.54 (t, J=5.3 Hz, 1H, aromatic), 7.41-7.25 (m, 4H, aromatic+NH$_2$), 7.25-7.16 (m, 3H, aromatic), 5.01 (p, J=7.3 Hz, 1H, CH), 4.61 (t, J=11.0 Hz, 1H, CH), 4.17 (dt, J=13.4, 6.5 Hz, 1H, CH), 3.16-3.00 (m, 3H, CH$_2$+CH), 2.92 (dt, J=15.8, 8.3 Hz, 1H, CH), 2.77 (t, J=7.7 Hz, 2H, CH$_2$), 1.86 (s, 3H, COCH$_3$), 1.67-1.53 (m, 1H, CH), 1.44 (tt, J=12.7, 6.0 Hz, 3H, CH$_2$+CH), 1.20 (dd, J=10.6, 7.3 Hz, 3H, CH$_3$).

$^{13}$C NMR (101 MHz, DMSO-d$_6$) δ (ppm)=213.71, 172.17, 166.88, 160.73, 157.11, 150.18, 134.19, 129.08, 128.83, 126.69, 52.99, 51.34, 49.87, 35.03, 29.04, 25.49, 22.87, 15.95.

Example 14

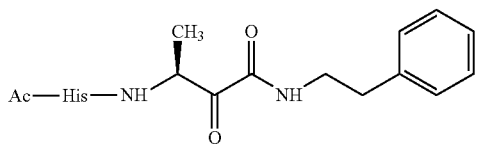

Compound 14

LC-MS analysis: One peak at 6.66 min, corresponding to [M+H]$^+$ 400.199 and [M+H$_2$O+H]$^+$ 418.21.

HR-MS: Monoisotopic mass: calculated 399.190654 for $C_{20}H_{25}N_5O_4$, found [M+H]$^+$ 400.19802 and [M+Na]$^+$ 422.17988.

$^1$H NMR (400 MHz, DMSO-d$_6$) δ (ppm)=14.16 (s, 1H, imidazole), 8.96 (s, 1H, aromatic), 8.76 (dt, J=11.7, 6.0 Hz, 1H, CONH), 8.49-8.38 (m, 1H, CONH), 8.21-8.11 (m, 1H, CONH), 7.38-7.25 (m, 3H, aromatic), 7.20 (d, J=8.7 Hz, 3H, aromatic), 5.04-4.94 (m, 1H, CH), 4.70-4.60 (m, 1H, CH), 3.10-2.97 (m, 1H, CH$_2$), 2.93-2.81 (m, 1H, CH$_2$), 2.77 (t, J=7.7 Hz, 2H, CH$_2$), 1.82 (d, J=3.7 Hz, 3H, COCH$_3$), 1.19 (dd, J=15.4, 7.3 Hz, 3H, CH$_3$).

$^{13}$C NMR (101 MHz, DMSO-d$_6$) δ (ppm)=193.52, 169.85, 160.86, 129.07, 128.81, 126.66, 51.35, 49.85, 35.03, 22.99, 15.89.

Example 15

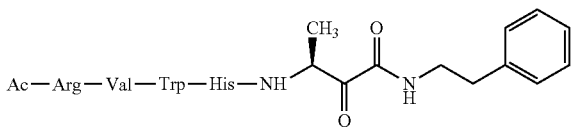

Compound 15

Example 16

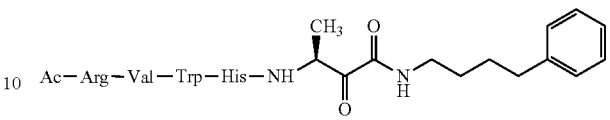

Compound 16

LC-MS: One peak at 7.75 min, corresponding to [M$_{mi}$+H]$^+$ 869.48.

HR MS: Monoisotopic mass: 868.47083, calcd. for $C_{44}H_{60}N_{12}O_7$, found [M$_{mi}$+H]$^+$ 869.47848 and [M$_{mi}$+Na]$^+$ 891.46039.

$^1$H NMR (401 MHz, DMSO-d$_6$) δ (ppm)=14.15 (s, 1H, NH imidazole), 10.81 (s, 1H, NH indole), 8.91 (s, 1H, aromatic), 8.77-8.66 (m, 1H, COCONH), 8.31 (t, J=7.3 Hz, 2H, CONH), 8.17-8.06 (m, 2H, CONH), 7.62 (d, J=8.9 Hz, 1H, aromatic), 7.55 (d, J=7.8 Hz, 2H, aromatic), 7.31 (d, J=8.0 Hz, 3H, CONH+aromatic), 7.30-7.21 (m, 3H, CONH+aromatic), 7.22-7.09 (m, 4H, aromatic), 7.14-7.11 (m, 1H, CONH) 7.05 (t, J=7.5 Hz, 1H, aromatic), 6.96 (t, J=7.4 Hz, 1H, aromatic), 5.08-4.94 (m, 1H, CH), 4.61 (d, J=6.5 Hz, 1H, CH), 4.51 (d, J=5.3 Hz, 1H, CH), 4.37-4.22 (m, 1H, CH), 4.22-4.09 (m, 1H, CH), 3.10 (dq, J=31.1, 6.7 Hz, 6H, CH$_2$), 2.92 (dt, J=15.1, 7.8 Hz, 2H, CH$_2$), 2.56 (t, J=7.4 Hz, 2H, CH$_2$), 2.00-1.90 (m, 1H, CH), 1.86 (s, 3H, COCH$_3$), 1.66-1.39 (m, 8H, CH$_2$), 1.23 (d, J=7.1 Hz, 3H, CH$_3$), 0.82-0.61 (m, 6H, CH$_3$).

$^{13}$C NMR (101 MHz, DMSO-d$_6$) δ (ppm)=196.41, 171.92, 171.39, 170.11, 142.49, 136.48, 128.72, 128.69, 126.14, 124.00, 110.16, 61.72, 57.35, 50.03, 35.15, 29.18, 28.76, 25.55, 22.94, 18.25, 16.08.

Biochemical and Biological Effects

Figure 2:
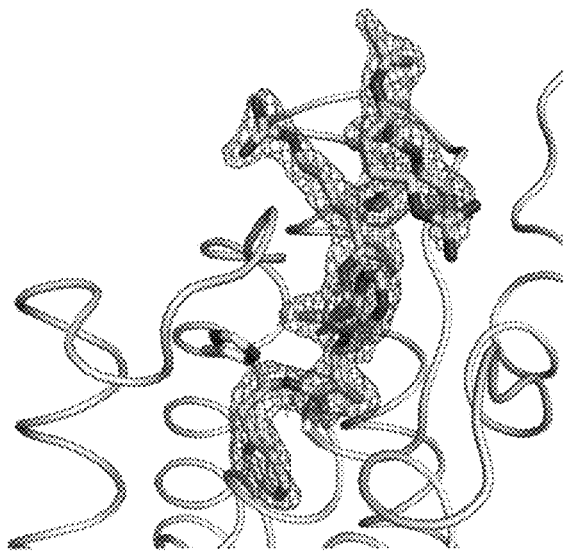
FIG. 2 shows the co-crystal structure of compounds 9 and 10 with the *E. coli* rhomboid protease GlpG. Catalytic dyad is shown in sticks, and the inhibitors in sticks surrounded by the 2mFo-DFc electron density map contoured at 1σ and shown 1.6 Å around the inhibitor model.
Figure 2:
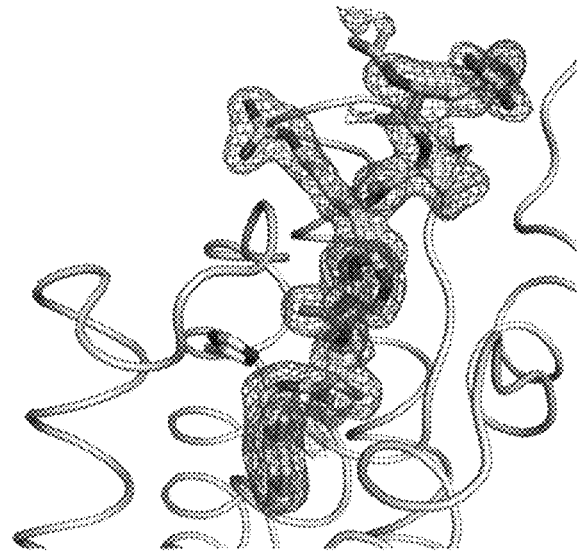
Figure 2:
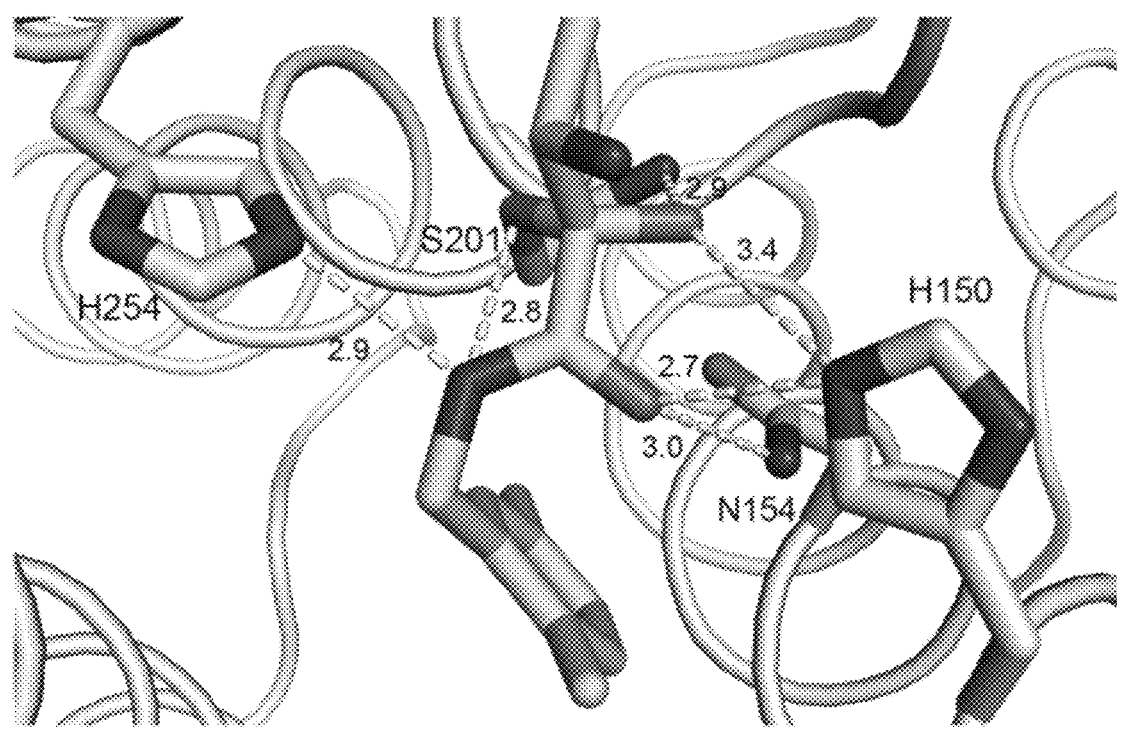
Figure 3:
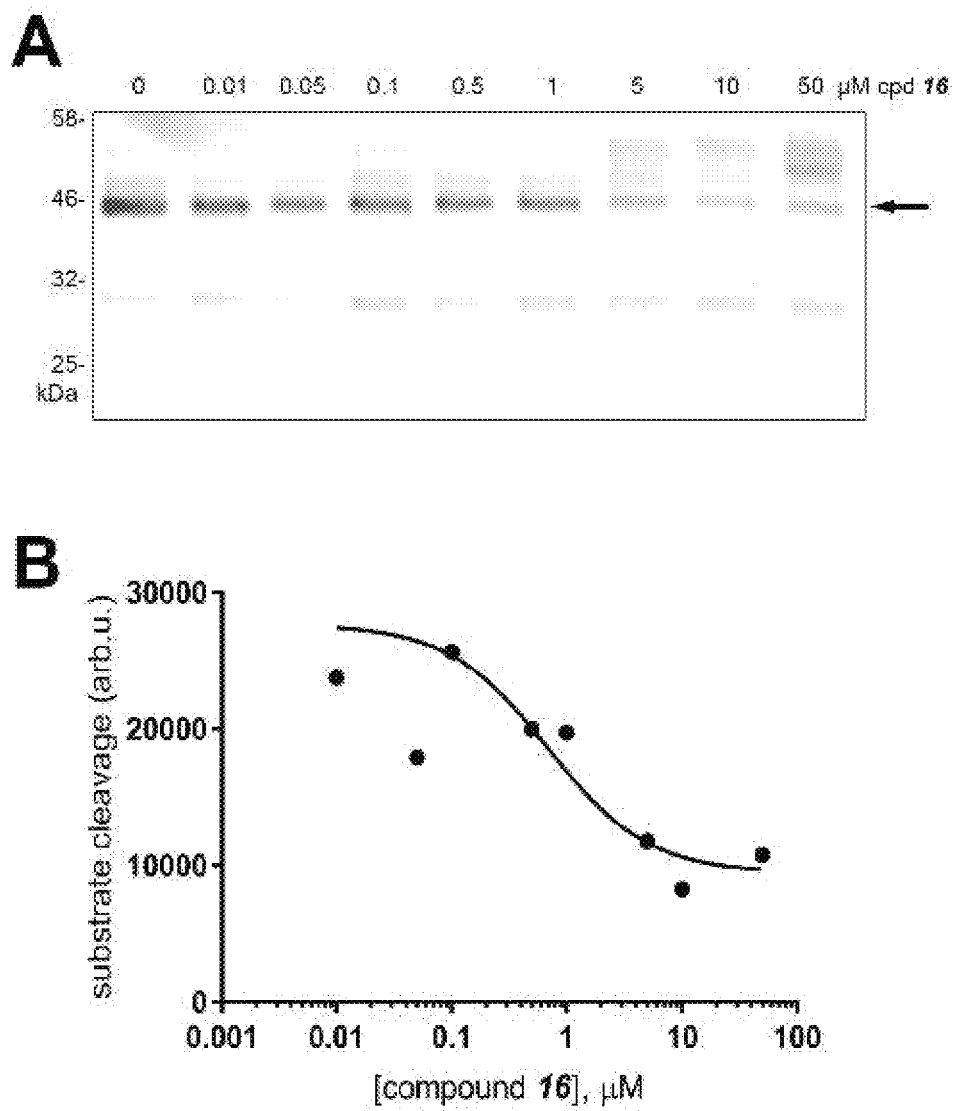
FIG. 3 shows the inhibition of *Plasmodium falciparum* rhomboid 4 (PfROM4) by Compound 16 in a cell culture assay. (A) HEK293ET cells were transfected with plasmids encoding PfROM4 and its substrate EBA175, and the shedding of EBA175 by PfROM4 into the medium under various concentrations of Compound 16 was quantitated by near-infrared fluorescence detected Western blotting. (B) Dose-response analysis of PfROM4 inhibition by Compound 16. The relative inhibition was evaluated by densitometry and analysed in GraphPad Prism, showing an inhibition curve with approximate IC50 in the micro- to submicromolar range.

The most effective compounds show inhibitory constants against the model rhomboid protease GlpG between 10 and 100 nM. The in vivo activity of the compounds against GlpG according to the invention is in the low nanomolar range (FIG. 1), which is up to three orders of magnitude better than any other currently used rhomboid inhibitors. The co-crystal structures of these compounds with rhomboid protease (FIG. 2) show their mode of binding into the active site of rhomboid. Without wishing to be bound by such a theory, it appears that the ketoamide warhead covalently bonds to the catalytic serine, and extensively hydrogen bonds throughout the active site. The tail at the ketoamide nitrogen interacts with the S2' pocket of rhomboid, engaging in a number of van der Waals contacts. Compound 16 inhibits *Plasmodium falciparum* rhomboid 4 (PfROM4), implicated in the invasion of the parasite into the host cells (Baker et al., 2006, Lin et al., 2013), in the cell culture at micromolar to submicromolar concentrations (FIG. 3)

TABLE 1

Influence of the peptidyl part and modification of the ketoamide substituent on the potency of the compounds. The IC$_{50}$ and K$_i$ values were measured in vitro as described (Ticha et al., 2017).

| Cpd No. | Structure | MW | IC$_{50}$ (µM) | K$_i$ Range (nM) |
|---|---|---|---|---|
| 1 | Ac-Arg-Val-Arg-His-NH-CH(CH$_3$)-C(O)-C(O)-NH$_2$ | 706.80 | 203 | — |
| 2 | Ac-Arg-Val-Arg-His-NH-CH(CH$_3$)-C(O)-C(O)-NH-iPr | 748.89 | 12.4 | — |
| 3 | Ac-Arg-Val-Arg-His-NH-CH(CH$_3$)-C(O)-C(O)-NH-cyclohexyl | 788.96 | 5.01 | — |
| 4 | Ac-Arg-Val-Arg-His-NH-CH(CH$_3$)-C(O)-C(O)-NH-CH$_2$-Ph | 796.94 | 7.64 | — |
| 5 | Ac-Arg-Val-Arg-His-NH-CH(CH$_3$)-C(O)-C(O)-NH-CH(CH$_3$)-Ph | 810.96 | 13.8 | — |
| 6 | Ac-Arg-Val-Arg-His-NH-CH(CH$_3$)-C(O)-C(O)-NH-CH$_2$-C(O)-O-Et | 792.90 | 4.24 | — |
| 7 | Ac-Arg-Val-Arg-His-NH-CH(CH$_3$)-C(O)-C(O)-NH-CH$_2$-C(CH$_3$)$_3$ | 776.95 | 2.15 | — |
| 8 | Ac-Arg-Val-Arg-His-NH-CH(CH$_3$)-C(O)-C(O)-NH-(CH$_2$)$_4$-CH$_3$ | 776.95 | 1.08 | — |
| 9 | Ac-Arg-Val-Arg-His-NH-CH(CH$_3$)-C(O)-C(O)-NH-CH$_2$-CH$_2$-Ph | 810.96 | 0.34 | 10-100 |

TABLE 1-continued

Influence of the peptidyl part and modification of the ketoamide substituent on the potency of the compounds. The $IC_{50}$ and $K_i$ values were measured in vitro as described (Ticha et al., 2017).

| Cpd No. | Structure | MW | $IC_{50}$ (μM) | $K_i$ Range (nM) |
|---|---|---|---|---|
| 10 | Ac-Arg-Val-Arg-His-NH-CH(CH₃)-C(O)-C(O)-NH-CH₂-(2,5-dimethylphenyl) | 824.99 | 0.18 | 10-100 |
| 11 | Ac-Arg-Val-Arg-His-NH-CH(CH₃)-C(O)-C(O)-NH-(CH₂)₃-phenyl | 839.02 | 0.15 | 10-100 |
| 12 | Ac-Val-Arg-His-NH-CH(CH₃)-C(O)-C(O)-NH-CH₂-CH₂-phenyl | 654.77 | 0.55 | — |
| 13 | Ac-Arg-His-NH-CH(CH₃)-C(O)-C(O)-NH-CH₂-CH₂-phenyl | 555.64 | 9.05 | — |
| 14 | Ac-His-NH-CH(CH₃)-C(O)-C(O)-NH-CH₂-CH₂-phenyl | 399.45 | 48.0 | — |
| 15 | | 841 | | |
| 16 | Ac-Arg-Val-Trp-His-NH-CH(CH₃)-C(O)-C(O)-NH-(CH₂)₃-phenyl | 869 | 0.77 | — |

INDUSTRIAL APPLICABILITY

The present inventions can be used in pharmaceutical industry. Namely, the described variations of peptidyl keto-amide inhibitors can be used as tools in cell-biological studies or as lead compounds in drug development against rhomboid proteases, in particular but not limited to the disease contexts of malaria, Parkinson's disease, cancer, diabetes or infections by pathogenic *Escherichia coli* or related bacteria.

LITERATURE REFERENCES

Bachovchin D A, Koblan L W, Wu W, Liu Y, Li Y, Zhao P, Woznica I, Shu Y, Lai J H, Poplawski S E, Kiritsy C P, Healey S E, DiMare M, Sanford D G, Munford R S, Bachovchin W W, Golub T R (2014) A high-throughput, multiplexed assay for superfamily-wide profiling of enzyme activity. *Nat Chem Biol* 10: 656-63

Baker R P, Wijetilaka R, Urban S (2006) Two *Plasmodium* rhomboid proteases preferentially cleave different adhesins implicated in all invasive stages of malaria. *PLoS Pathog* 2: e113

Cao H, Liu H, Domling A (2010) Efficient multicomponent reaction synthesis of the schistosomiasis drug praziquantel. *Chemistry* 16: 12296-8

De Risi C, Pollini G P, Zanirato V (2016) Recent Developments in General Methodologies for the Synthesis of alpha-Ketoamides. *Chem Rev* 116: 3241-305

Dickey S W, Baker R P, Cho S, Urban S (2013) Proteolysis inside the membrane is a rate-governed reaction not driven by substrate affinity. *Cell* 155: 1270-81

Hudlicky M (1990) *Oxidations in organic chemistry*. American Chemical Society, Washington, D.C.

Chan E Y, McQuibban G A (2013) The mitochondrial rhomboid protease: Its rise from obscurity to the pinnacle of disease-relevant genes. *Biochim Biophys Acta* 1828: 2916-25

Cho S, Dickey S W, Urban S (2016) Crystal Structures and Inhibition Kinetics Reveal a Two-Stage Catalytic Mechanism with Drug Design Implications for Rhomboid Proteolysis. *Mol Cell* 61: 329-340

Lin J W, Meireles P, Prudencio M, Engelmann S, Annoura T, Sajid M, Chevalley-Maurel S, Ramesar J, Nahar C, Avramut C M, Koster A J, Matuschewski K, Waters A P, Janse C J, Mair G R, Khan S M (2013) Loss-of-function analyses defines vital and redundant functions of the *Plasmodium* rhomboid protease family. *Mol Microbiol* 88: 318-38

Lloyd-Williams P, Albericio F, Giralt E (1997) *Chemical approaches to the synthesis of peptides and proteins*. CRC Press, Boca Raton Meissner C, Lorenz H, Hehn B, Lemberg M K (2015) Intramembrane protease PARL defines a negative regulator of PINK1- and PARK2/Parkin-dependent mitophagy. *Autophagy* 11: 1484-98

O'Donnell R A, Hackett F, Howell S A, Treeck M, Struck N, Krnajski Z, Withers-Martinez C, Gilberger T W, Blackman M J (2006) Intramembrane proteolysis mediates shedding of a key adhesin during erythrocyte invasion by the malaria parasite. *J Cell Biol* 174: 1023-33

Pierrat O A, Strisovsky K, Christova Y, Large J, Ansell K, Bouloc N, Smiljanic E, Freeman M (2011) Monocyclic beta-lactams are selective, mechanism-based inhibitors of rhomboid intramembrane proteases. *ACS Chem Biol* 6: 325-35

Ruiz N, Falcone B, Kahne D, Silhavy T J (2005) Chemical Conditionality. *Cell* 121: 307-317

Russell C W, Richards A C, Chang A S, Mulvey M A (2017) The Rhomboid Protease GlpG Promotes the Persistence of Extraintestinal Pathogenic *Escherichia coli* within the Gut. *Infect Immun* 85

Semple J E, Owens T D, Nguyen K, Levy O E (2000) New synthetic technology for efficient construction of alpha-hydroxy-beta-amino amides via the Passerini reaction. *Org Lett* 2: 2769-72

Song W, Liu W, Zhao H, Li S, Guan X, Ying J, Zhang Y, Miao F, Zhang M, Ren X, Li X, Wu F, Zhao Y, Tian Y, Wu W, Fu J, Liang J, Wu W, Liu C, Yu J et al. (2015) Rhomboid domain containing 1 promotes colorectal cancer growth through activation of the EGFR signalling pathway. *Nat Commun* 6: 8022

Souček M, Urban J (1995) An Efficient Method for Preparation of Optically Active N-Protected α-Amino Aldehydes from N-Protected α-Amino Alcohols. *Collect Czech Chem Commun* 60: 693-696

Strisovsky K (2013) Structural and mechanistic principles of intramembrane proteolysis—lessons from rhomboids. *FEBS J* 280: 1579-603

Strisovsky K (2016) Rhomboid protease inhibitors: Emerging tools and future therapeutics. *Semin Cell Dev Biol* 60: 52-62

Strisovsky K, Sharpe H J, Freeman M (2009) Sequence-specific intramembrane proteolysis: identification of a recognition motif in rhomboid substrates. *Mol Cell* 36: 1048-59

Ticha A, Stanchev S, Skerle J, Began J, Ingr M, Svehlova K, Polovinkin L, Ruzicka M, Bednarova L, Hadravova R, Polachova E, Rampirova P, Brezinova J, Kasicka V, Majer P, Strisovsky K (2017) Sensitive Versatile Fluorogenic Transmembrane Peptide Substrates for Rhomboid Intramembrane Proteases. *J Biol Chem* 292: 2703-2713

Venkatraman S, Bogen S L, Arasappan A, Bennett F, Chen K, Jao E, Liu Y T, Lovey R, Hendrata S, Huang Y, Pan W, Parekh T, Pinto P, Popov V, Pike R, Ruan S, Santhanam B, Vibulbhan B, Wu W, Yang W et al. (2006) Discovery of (1R,5S)—N-[3-amino-1-(cyclobutylmethyl)-2,3-dioxopropyl]-3-[2(S)-[[[(1,1-dimethylethyl)amino]carbonyl]amino]-3,3-dimethyl-1-oxobutyl]-6,6-dimethyl-3-azabicyclo[3.1.0]hexan-2(S)-carboxamide (SCH 503034), a selective, potent, orally bioavailable hepatitis C virus NS3 protease inhibitor: a potential therapeutic agent for the treatment of hepatitis C infection. *J Med Chem* 49: 6074-86

Vosyka O, Vinothkumar K R, Wolf E V, Brouwer A J, Liskamp R M, Verhelst S H (2013) Activity-based probes for rhomboid proteases discovered in a mass spectrometry-based assay. *Proc Natl Acad Sci USA* 110: 2472-7

Wang Y, Zhang Y, Ha Y (2006) Crystal structure of a rhomboid family intramembrane protease. *Nature* 444: 179-80

Wolf E V, Zeissler A, Vosyka O, Zeiler E, Sieber S, Verhelst S H (2013) A new class of rhomboid protease inhibitors discovered by activity-based fluorescence polarization. *PLoS One* 8: e72307

Wuts P G M, Greene T W, Greene T W (2014) *Greene's protective groups in organic synthesis*. John Wiley & Sons, Inc., Hoboken, N.J.

Yin J, Gallis C E, Chisholm J D (2007) Tandem oxidation/halogenation of aryl allylic alcohols under Moffatt-Swern conditions. *J Org Chem* 72: 7054-7

Zoll S, Stanchev S, Began J, Skerle J, Lepsik M, Peclinovska L, Majer P, Strisovsky K (2014) Substrate binding and specificity of rhomboid intramembrane protease revealed by substrate-peptide complex structures. *EMBO J* 33: 2408-21

The invention claimed is:

1. A compound having the formula (I)

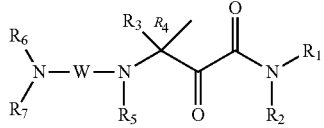

(I)

wherein $R_1$ is selected from the group consisting of H, alkyl, haloalkyl, alkenyl, alkynyl, aryl, arylalkyl, cycloalkyl, cycloalkylalkyl, cycloalkenyl, cycloalkenylalkyl, heterocyclyl, heterocyclylalkyl, heteroaryl and heteroarylalkyl, each optionally substituted with from 1 to 3 substituents independently selected from the group consisting of alkyl, cyano, halo, oxo, nitro, hydroxyl, —O(alkyl), —NH$_2$, —N(H)(alkyl), —N(alkyl)$_2$, —S(alkyl), —S(O)(alkyl), —SO$_2$alkyl, —NHCONH$_2$, —CO$_2$H, —CO$_2$(alkyl), —COalkyl, —CONH$_2$, —CONHalkyl, and —CON(alkyl)$_2$;

$R_2$ and $R_5$ are selected from hydrogen and alkyl;

$R_3$ and $R_4$ are independently selected from the group consisting of hydrogen, alkyl, haloalkyl, alkenyl, alkynyl, aryl, arylalkyl, cycloalkyl, cycloalkylalkyl, cycloalkenyl, cycloalkenylalkyl, heterocyclyl, heterocyclylalkyl, heteroaryl and heteroarylalkyl; or, taken together with the carbon atom to which they are attached, form $R_3$ and $R_4$ form a cycloalkyl or heterocyclyl ring; wherein each $R_3$ and $R_4$, is independently optionally substituted with from 1 to 3 substituents independently selected from the group consisting of alkyl, cyano, halo, oxo, nitro, hydroxyl, —O(alkyl), —NH$_2$, —N(H)(alkyl), —N(alkyl)$_2$, —S(alkyl), —S(O)(alkyl), —SO$_2$alkyl, —NHCONH$_2$, —CO$_2$H, —CO$_2$(alkyl), —COalkyl, —CONH$_2$, —CONHalkyl, —CON(alkyl)$_2$;

or, taken together with the atoms to which they are attached, $R_1$ and $R_2$ or $R_1$ and $R_3$ form a heterocyclyl ring;

$R_6$ and $R_7$ are independently selected from the group consisting of hydrogen, alkyl, cycloalkyl, acyl, aryl, heteroaryl, and heterocyclyl; or, taken together with the nitrogen atom to which they are attached, $R_6$ and $R_7$ form a heterocyclyl ring;

W represents a group (Aaa)$_m$-Arg-His or (Aaa)$_m$-Trp-His; and m represents an integer of from 0 to 18;

or a pharmaceutically acceptable salt, ester or prodrug thereof.

2. A compound according to claim 1 having the formula (II)

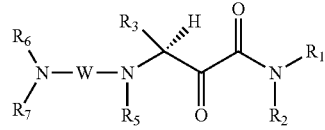

(II)

wherein $R_3$ is $C_1$-$C_6$alkyl; and $R_1$, $R_2$, $R_5$-$R_7$ and W have the meanings as described in claim 1.

3. The compound according to claim 2, where $R_3$ is methyl.

4. A compound according to claim 1, wherein $R_2$ is hydrogen.

5. A compound according to claim 1, wherein $R_1$ is selected from the group consisting of alkyl, cycloalkyl, arylalkyl optionally substituted on the aryl ring with from 1 to 3 $C_1$-$C_3$ alkyl substituents, and alkoxycarbonylalkyl.

6. A compound according to claim 1, wherein W represents a group (Aaa)$_q$-Arg-Val-Arg-His (SEQ ID NO. 1) or (Aaa)$_q$-Arg-Val-Trp-His (SEQ ID NO. 2); wherein q represents an integer of from 0 to 16.

7. A compound according to claim 1, wherein $R_6$ is acyl.

8. The compound according to claim 7, where $R_6$ is acetyl.

9. A compound according to claim 1, wherein $R_7$ is hydrogen.

10. A compound which is one of

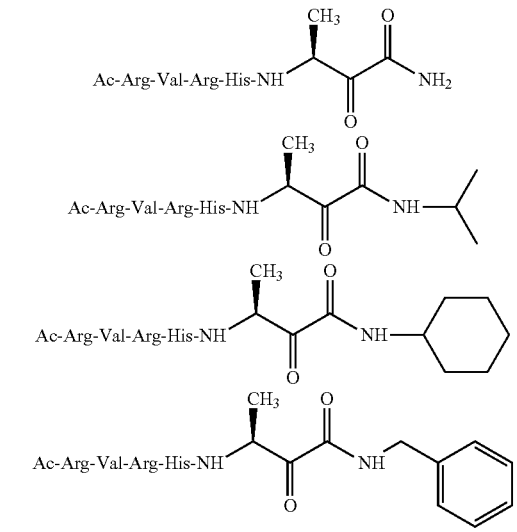

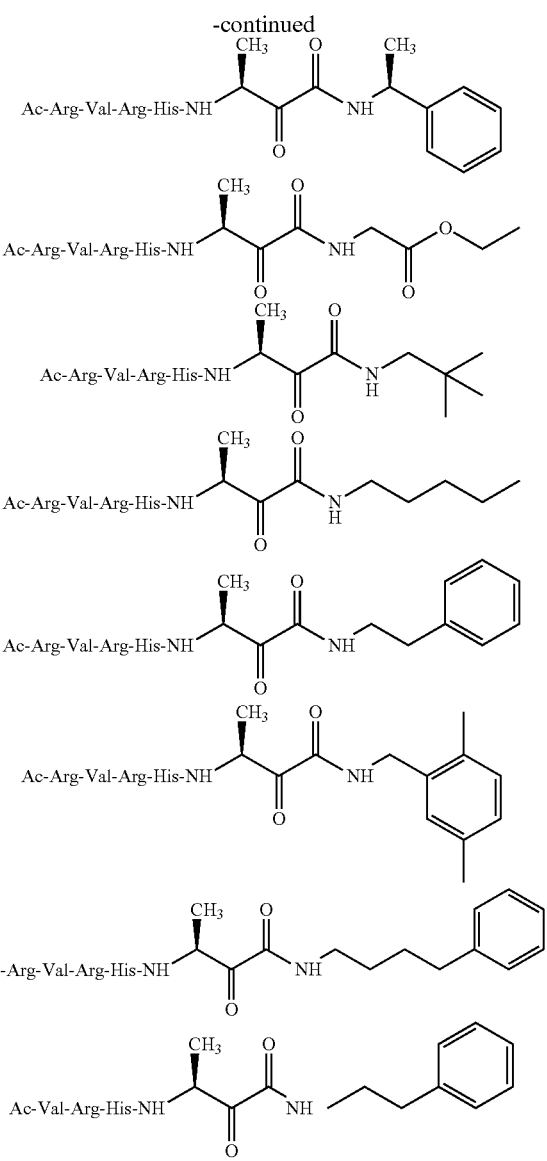

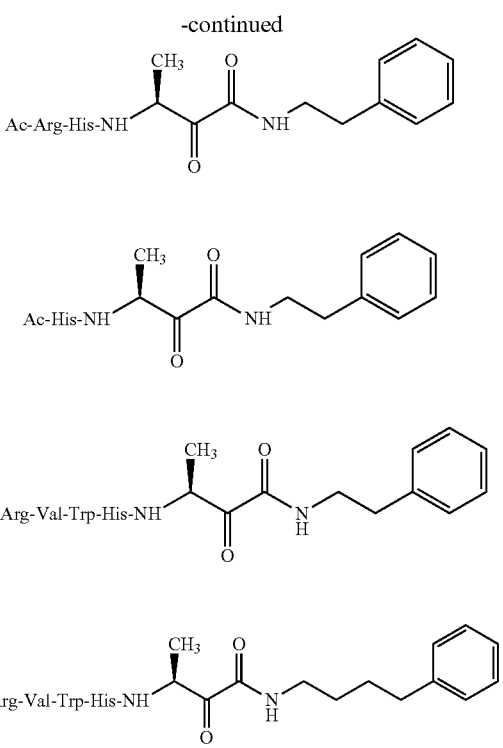

11. A pharmaceutical composition comprising a compound according to claim 1 together with a pharmaceutically acceptable excipient.

12. A method of treating a condition selected from the group consisting of malaria, cancer, Parkinson's disease, type 2 diabetes, and bacterial infection comprising the step of administering the compound of claim 1 to a subject in need thereof.

13. A method of inhibiting activity of a rhomboid protease present in a cell, comprising contacting said cell with an effective amount of the compound of claim 1.

14. The method according to claim 13 wherein the rhomboid protease is GlpG.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: peptide sequence W, first preferred embodiment

<400> SEQUENCE: 1

Arg Val Arg His
1
```

```
<210> SEQ ID NO 2
<211> LENGTH: 4
<212> TYPE: PRT
<213> ORGANISM: Artificial
<220> FEATURE:
<223> OTHER INFORMATION: peptide sequence W, second preferred embodiment

<400> SEQUENCE: 2

Arg Val Trp His
1
```